(12) United States Patent
Prahl et al.

(10) Patent No.: US 7,112,346 B2
(45) Date of Patent: *Sep. 26, 2006

(54) METHOD OF INDUCING MALOLACTIC FERMENTATION IN WINE OR FRUIT JUICE BY DIRECT INOCULATION WITH A NON-ACTIVATED STARTED CULTURE

(75) Inventors: Claus Prahl, Graested (DK); Jan Clair Nielsen, Hundested (DK)

(73) Assignee: Chr. Hansen A/S, Horsholm (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 327 days.

(21) Appl. No.: 08/811,057

(22) Filed: Mar. 3, 1997

(65) Prior Publication Data

US 2003/0203069 A1 Oct. 30, 2003

Related U.S. Application Data

(63) Continuation-in-part of application No. 08/039,317, filed as application No. PCT/DK93/00116 on Mar. 30, 1993, now Pat. No. 5,607,854, which is a continuation-in-part of application No. 07/864,823, filed on Apr. 1, 1992, now abandoned.

(51) Int. Cl.
*C12G 1/022* (2006.01)

(52) U.S. Cl. ........................................ 426/15
(58) Field of Classification Search ............. 426/13, 426/15, 51
See application file for complete search history.

(56) References Cited

U.S. PATENT DOCUMENTS

| | | | | |
|---|---|---|---|---|
| 4,547,373 A | 10/1985 | Sandine | | 426/15 |
| 4,562,077 A | 12/1985 | King | | 426/13 |
| 5,077,060 A | 12/1991 | Prahl | | 426/15 |
| 5,460,837 A | 10/1995 | D'Amice et al. | | 426/11 |
| 5,607,854 A | 3/1997 | Prahl et al. | | 435/252.1 |

FOREIGN PATENT DOCUMENTS

| | | |
|---|---|---|
| AU | 92/13009 | 10/1992 |
| EP | 0 141 878 | 11/1983 |
| EP | 0 523 316 | 1/1993 |
| FR | 2 485 037 | 6/1981 |
| WO | 89/06685 | 7/1989 |

OTHER PUBLICATIONS

Amerine et al, Methods of Analysis of Most & Wire, John Wiley & Bros., New York, 1980, pp. 47, 48 and 62.
B. Krieger et al., "Techniques for the Application of Starter Cultures Used for Malolactic Fermentation in Wine", Food Biotechnol., vol. 7, (1990), pp. 484.
J. Silver et al., "Control of Malolactic Fermentation in Wine. 2. Isolation and Characterization of a New Malolactic Organism", Am. J. Enol. Vitic., vol. 32, No. 1, (1981), pp. 64–72.
C. Davis et al., "Occurrence and Properties of Bacteriophases of Leuconostoo–oenos in Australian Wines", Appl. Environ. Microbio., vol. 4, (1985), [abstract].
T.J. Britz et al., "The Combination Effect of PH Sulfur Dioxide Ethanol and Temperature on the Growth of Leuconostoc–oenos", J. Appl. Bacteriol., vol. 1, (1990), [abstract].
WPI Abstract, Acc No. 090–060417, JP 2086765, Date Sep. 1988.
C.R. Davis et al., "Growth and Metabolismof Lactic–Acid Bacteria During and After Malolactic Fermentation of Wines at Different PH", Appl. Environ. Microbiol., vol. 3, (1986), [Abstract].
"Proc. UC Davis Grape & Wine Centennial Symposium", Robert Beelman, Development And Utilization Of Starter Cultures To Induce Malolactic Fermentation In Red Table Wines (pp. 109–117).

*Primary Examiner*—Keith Hendricks
(74) *Attorney, Agent, or Firm*—Beth A. Burrous; Foley & Lardner LLP

(57) ABSTRACT

A selected malolactically active *Ln. oenos* strain which is useful for inducing malolactic fermentation in wine or fruit juice by the direct inoculation of a concentrate of a starter culture containing the strain, the strain having a survival rate of at least 80% when inoculated directly into a wine having a pH of 3.2 or lower and containing at least 25 mg $SO_2$ per l and at least 12 vol % ethanol, and capabl, of starting malolactic fermentation when added directly to the wine or fruit juice at a concentration of less than $10^7$ colony forming units per ml. There is also provided a method of isolating such a strain and a method for producing a culture of the strain.

23 Claims, 17 Drawing Sheets

METHOD OF INDUCING MALOLACTIC FERMENTATION IN WINE OR FRUIT JUICE BY DIRECT INOCULATION WITH A NON-ACTIVATED STARTED CULTURE

This application is a continuation-in-part of U.S. Ser. No. 08/039,317, filed Jul. 2, 1993 (now U.S. Pat. No. 5,607,854), which is a continuation-in-part of Ser. No. 07/864,823, filed Apr. 1, 1992 (abandoned) and this application is a national phase application of PCT application PCT/DK93/00116, filed Mar. 30, 1993.

FIELD OF INVENTION

The present invention provides a novel method of inducing the decarboxylation of malic acid to lactic acid in wine or fruit juice by direct inoculation with a non-activated starter culture of malolactically active lactic acid bacteria and a composition comprising bacteria useful in the method.

BACKGROUND OF THE INVENTION

Grape juice, must and other fruit juice contain a varying amount of L-malic acid and L-malate, the amount typically being in the range of 1 to 10 g/l. The amount of malic acid and malate depends largely on the climatic conditions prevailing in the viticultural region. Hence, wines produced in colder areas tend to have a relatively higher acid content, since the malic acid is not degraded during the normal alcoholic fermentation. From a taste and flavor point of view, malic acid is considered undesirable in most red wines and in several types of rose wines, white wines or sparkling wines.

However, the content of malic acid and malate in a wine may be reduced by a so-called malolactic fermentation (MLF) of the wine which fermentation results from the metabolic activity of various lactic acid bacteria, including species belonging to the genera of Lactobacillus, Pediococcus and Leuconostoc. Such bacteria may be present in must and wine as part of the indigenous microbial flora hereof, or they may have been added as a bacterial starter culture. Typically, the MLF is associated with malolactic bacterial growth and catabolic processes during which the wine acidity is reduced. The catabolic phase is usually entered when the malolactically active bacteria during the growth phase has reached a population density of about $10^6$ colony forming units (CFU) per ml. The microbial malolactic deacidification results from the decarboxylation of the dicarboxylic acid, L-malic acid to the monocarboxylic acid, L-lactic acid. As a result of this malolactic fermentation, the acidity of the wine decreases and the pH increases, resulting in a wine with a softer palate relative to that of the wine before the malolactic fermentation. Following a successful malolactic fermentation in wine, no further microbial growth will normally occur and hence, the wine is considered to be microbiologically stable.

The malolactic fermentation may occur spontaneously in the wine as a result of the growth of an indigenous flora of malolactically active lactic acid bacteria originating from the vines and grape skins and also often surviving from one season to the next on winery equipment, especially wooden casks or other equipment made of wood. When occurring in this fashion, malolactic fermentation is often delayed and may take place several months after the alcoholic fermentation. The initial number of bacteria is often quite small and the environment of the wine is frequently rather hostile to the growth of these bacteria due to the content of ethanol and sulphur dioxide in the wine, as well as its low pH and low nutrient concentration. The extended lag phase of the malolactic bacteria during which the wine is biologically unstable may result in the growth of bacteria producing volatile acidity and hence spoilage of the wine. Apart from this, certain indigenous malolactic bacteria spontaneously growing in the wine may produce certain compounds, e.g. biogenic amines that are believed to give rise to health problems.

In the traditional winery industry where the spontaneously occurring malolactic fermentation is being relied upon, it is common practice to stimulate malolactic fermentation by reducing the amount of added sulphur when determined as sulphur dioxide, to below 50 mg per l, delaying the removal of the lees, increasing the temperature of the wine to above 20° C., or ensuring a pH of more than 3.4. These measures, however, may also favor the growth of undesired microorganisms in the wine such as *Acetobacter* species, thus increasing the likelihood of wine spoilage, and this approach therefore requires extremely careful supervision of the decarboxylation process. Even if precautions are taken to enhance spontaneous MLF, this process is still difficult, not to say impossible, to control, and its occurrence has become even more unpredictable as winery hygiene has improved e.g. as a result of the replacement of wooden casks with stainless steel tanks. Such hygienic measures serve to ensure a uniform quality of the wine and reduce the risk of spoilage. However, they also reduce the chance of spontaneous conversion of malic acid taking place in the wine.

For this reason, and because the winemaker will often prefer to exercise a greater degree of control over the malolactic fermentation process it has become increasingly common practice in the winery industry to add a starter culture of malolactically active bacteria to the wine after the alcoholic fermentation. Presently, such a postfermentation malolactic fermentation in wine may be induced in different ways.

Currently, a widely practiced method of inducing MLF is to seed a wine with a small proportion of another wine already undergoing MLF and thus containing a high number of viable malolactically active bacteria. The culture in the seed wine is then already well adapted to wine conditions and will usually be capable of completing the malolactic fermentation in the seeded wine. However, this method of inoculation is rather tedious and not completely controllable. Thus, the method requires that a concentrated "mother culture" of the bacteria is propagated for an extended period of time, such as about two months, in diluted wine or grape juice, optionally after rehydration and/or adaptation of the mother culture in e.g. a grape fruit juice-containing medium which is then used to inoculate the wine to be used as a bulk starter culture in the form of seed wine. Typically, the wine is inoculated with the seed wine at a rate of 1 to 10 vol %, and accordingly, this method requires substantial investments in propagation equipment and adequately trained staff. In addition, it is difficult to control the propagation process and hence serious timing problems may occur.

Should both red and white wine starter cultures be required these problems are doubled.

Relative to the above practice of using a seed wine, a post-fermentation inoculation of wine with concentrated freeze-dried or frozen starter cultures of malolactically active lactic acid bacteria implies considerable savings in time and labor by substantially reducing the amount of scale-up work required. Such concentrated starter cultures are now commercially available and their use is being increasingly accepted in the wine industry, although their malolactic effect is not completely reliable. These culture compositions may be concentrated to contain a number of colony forming units which, when determined in a non-inhibitory medium is in the range of $10^9$ to $10^{11}$ per g of culture.

However, the use of known, commercially available malolactically active culture compositions contain bacteria which are susceptible to the conditions (low pH, content of $SO_2$, content of ethanol) prevailing in the fermented wine and accordingly, their malolactic efficiency requires that they become adapted to the hostile conditions in the wine by carrying out a thawing and rehydration step (if freeze-dried), a thawing step (if frozen) and an activation step prior to inoculation in the wine. This requirement is assumingly due to the well-known phenomenon that a freeze-dried or frozen lactic acid bacterial culture composition, even if it includes additives protecting the bacteria against cell damages, will as a result of the freezing and/or freeze-drying process have an increased susceptibility to low pH, $SO_2$, ethanol and low temperatures as compared to a freshly grown culture of the same species.

If not rehydrated and activated as described above, the survival rate of the known commercial malolactic compositions on direct inoculation into wine will typically be in the range of 0.01 to 1% or even lower. Furthermore, the initially surviving non-adapted bacteria may gradually lose their viability in the wine.

Typically, this required adaptation comprises an initial thawing and/or rehydration process, the latter comprising dissolving the freeze-dried composition in water and adding various nutrients such as a sugar, vitamins, minerals or yeast extract and keeping the resulting solution at about 22° C. for about one hour. Subsequently, the thus rehydrated composition is subjected to an activation step, typically lasting 48 to 84 hours, in a medium which typically comprises grape juice or wine diluted with water, yeast extract, trace elements and vitamins. Normally, the number of CFUs does not increase during this activation period, on the contrary, the number may decrease. Even if the starter culture composition is adapted as described above, a varying proportion of adapted bacteria may lose viability as determined in a non-inhibitory medium when inoculated in wine. This loss of viability may be up till 90% of the added number of CFUs.

In EP-A1-0141878 is disclosed a method of reducing malic acid to lactic acid in wine by the introduction of high numbers of bacterial cells into the wine, which method comprises activating a concentrate of a bacterial culture in a nitrogen source-augmented fruit juice to form an activated mixture of bacteria containing at least about $10^5$ CFUs per ml and introducing the activated mixture into wine or grape must and converting the malic acid to lactic acid. The activation conditions disclosed are an activation period of 48 hours at 24° C.

Krieger et al. (Food Biotechnol. 1990, 7, 484) have disclosed the application in wine of malolactically active strains of *Leuconostoc oenos* (*Ln. oenos*) and *Lactobacillus* spp. in the form of fresh or frozen concentrates using direct inoculation, i.e. without preceding activation, of at least $10^7$ CFUs per ml which concentration is indicated as being necessary to start malolactic fermentation. However, the application of such a high concentration of malolactically active organisms is not commercially feasible in the wine industry due to the high cost of starter cultures. The necessity to apply at least $10^7$ CFUs per ml as disclosed in order to start MLF may indicate that the survival rate of these organisms when applied directly to the wine is so low that a malolactically active concentration of the organisms is only achieved at the indicated inoculation level.

The present invention provides, compared to the known methods, a significantly improved method of inducing malolactic fermentation in wine or fruit juice whereby it has become possible to achieve an effective malolactic fermentation herein within a short period of time by inoculating wine or a fruit juice directly with a concentrated culture composition of malolactically active bacteria at an economically feasible concentration and accordingly, to avoid the tedious and costly processes of rehydration, activation, adaptation and/or expansion which are currently required with commercial malolactically active starter cultures.

SUMMARY OF THE INVENTION

Accordingly, the present invention relates in a first aspect to a selected *Ln. oenos* strain which is malolactically active in wine or fruit juice, the strain having at least one of the following characteristics when it in a frozen or freeze-dried state is added directly to wine without any preceding activation, adaptation and/or expansion step:
(i) a survival rate which is in the range of 90% to 100% in a wine at a temperature in the range of 18 to 21° C., said wine having an ethanol content in the range of 10.5 to 13 vol %, a pH in the range of 3.2 to 3.6 and a content of $SO_2$ which is in the range of 0 to 26 mg per l, or
(ii) a survival rate of at least 50% in a malic acid-containing wine having a pH of 3.2 or lower and containing at least 25 mg $SO_2$ per l and at least 12 vol % ethanol, or
(iii) a survival rate which is in the range of 80% to 100% after 2 days at a temperature of 20° C. in a wine prepared by yeasting a sterile Riesling grape fruit juice without the addition of sulphite, the wine containing 11.5 vol % ethanol, 3.9 g/l of malic acid, 3.5 g/l of residual sugar and having a pH of 3.15.

In one preferred embodiment the above selected strain is one which, when it is added to a wine or fruit juice in a frozen or freeze-dried state at a concentration of CFUs which is in the range of $1 \times 10^6$ to $5 \times 10^7$ per ml of the wine or fruit juice, is capable of reducing at least 4 g of malic acid per l of wine or fruit juice to less then 0.5 g per l within a period of time which is at the most 15 days, said strain having at least one of following characteristics:
(a) capable of decarboxylating malic acid in wine at a pH of 3.2 or lower,
(b) capable of decarboxylating malic acid in wine in the presence of 25 mg $SO_2$ per l or more, and (c) capable of decarboxylating malic acid in wine having an ethanol content of 10 vol % or higher.
(d) a survival rate of at least 80% when introduced directly into a wine having a pH of 3.2 or lower and containing at least 10 vol % ethanol,
(e) a survival rate of at least 50% when introduced directly into a wine having a pH of 3.2 or lower and containing at least 25 mg $SO_2$ per l and at least 12 vol % ethanol,
(f) resistant to attack by bacteriophages,
(g) capable of retaining at least one of the characteristics (a) through (f) during propagation and concentration.

In a further aspect of the invention there is provided a method of converting malic acid in a wine or a fruit juice to lactic acid, comprising adding directly to said wine or fruit juice a frozen or freeze-dried composition comprising the above selected strain, without any preceding activation, adaptation and/or expansion of the composition and keeping the wine or the fruit juice under conditions which allow conversion of the malic acid, to obtain a malolactically fermented wine or fruit juice having a content of malic acid which is at the most 0.5 g per l.

In a still further aspect, the invention relates to a concentrate of one or more of the selected strains of malolactically active bacteria as defined herein, and in another aspect there is provided a malolactic starter culture composition comprising a concentrate of selected malolactically active bacterial strain(s), as defined herein and at least one further ingredient selected from cryoprotectants, bacterial nutrients and bulking agents.

In a still further aspect, the invention provides a method of isolating a Ln. oenos strain as defined above, the method comprising:
(i) isolating malolactically active Ln. oenos strains from wine,
(ii) combining in a first selection step a plurality of such isolated strains and subjecting these to a cultivation in a turbidostat fermenter operated for up to 6 weeks at a temperature in the range of 15–35° C. using as the growth medium a wine having a pH which is below 4 and an ethanol content which is in the range of 10–15% (v/v), and isolating from said growth medium one or more acid and ethanol tolerant strains,
(iii) selecting in a second selection step such acid and ethanol tolerant strains having at least one of the following characteristics selected from the group consisting of (a) malolactically active in wine having a pH of 3.2 or lower, (b) malolactically active in wine in the presence of 25 mg $SO_2$ per l or more, (c) malolactically active in a wine having an ethanol content of 10% (v/v) or higher, (d) a survival rate as defined herein of at least 50% when introduced into a wine or fruit juice having a pH of 3.2 or lower and containing at least 25 mg $SO_2$ per l and at least 12 vol % ethanol and (e) resistant to attack by bacteriophages,
(iv) subjecting in a third selection step one or more strains selected in step (iii) to propagation conditions, and selecting strains which under such conditions can be propagated to at least $1 \times 10^9$ CFU/ml and which has retained at least one of the characteristics (a) through (e), and
(v) subjecting in a fourth selection step such selected strains to a down-stream process including at least one of the following steps: harvesting of cells from the propagation medium, concentration of the cells, freezing of the concentrate or freeze-drying.

The invention also pertains to a method of producing a culture of Ln. oenos strain, the method comprising propagating the strain in a medium having an initial pH which is in the range of 3.5 to 4.5, said medium having a composition permitting the propagation to occur at a pH being at the most 4 for at least 2 hours, harvesting the cells, concentrating the cells and optionally freezing or freeze-drying the cells.

DETAILED DISCLOSURE OF THE INVENTION

The present invention relates in one aspect to a novel method of inducing the decarboxylation of malic acid to lactic acid in wines and fruit juices by direct inoculation of the wine or fruit juice with appropriately selected malolactically active bacteria.

In the present context, the term "wine" is used to describe a product resulting from an alcoholic fermentation of juice or must of grapes or of any other fruit or berries, whether the fermentation occurs spontaneously or it is obtained by the addition of a yeast culture.

A wine made from grapes may be a red wine, a white wine, a rosé wine, all of which may be in the form of sparkling wines.

The conditions prevailing in wine at the completion of the alcoholic fermentation are generally unfavourable for microbial growth. These adverse conditions include a pH typically being in the range of 2.8 to 4.0 such a pH of 3.2 or lower, an ethanol content which is typically in the range of 8 to 14 vol %, such as in the range of 10 to 12 vol %, a low content of nutrients such as carbon sources due to the depletion of the nutrients during the alcoholic fermentation. In addition, a sulphur-containing substance may have been added as a preservative to the must in an amount which is typically in the range of 5 to 70 mg per l including amounts of 25 mg of $SO_2$ as defined below per l in the fermented wine, or higher.

In this connection it should be noted that the addition of sulphur-containing substances to must is conventionally carried out by the addition of a sulphite or another water soluble sulphur-containing substance. In the fermenting must the sulphite is at least partially converted to $SO_2$, the extent of the conversion depending i.a. on the pH. Part of the generated $SO_2$ will be in the form of free molecules and part will be bound. In the art, the content of sulphur in must or wine is determined by measuring the total content of sulphur-containing substances as total $SO_2$. Accordingly, when used herein the term "$SO_2$" denotes the total content of sulphur determined according to the Rebelein method in which all sulphur-containing substances are converted to $SO_2$ before the measuring step.

These conditions in the wine, singly and in combination provide a rather hostile environment for bacteria, including malolactically active lactic acid bacteria. Such bacteria are primarily organisms belonging to the genera of Leuconostoc, Lactobacillus and Pediococcus. Among these genera of naturally occurring malolactically active bacteria, organisms belonging to Leuconostoc are generally most tolerant to low pH and they may grow at pH values below 3.3. At more moderate pH values such as pH of 3.6 and above, species of Lactobacillus and Pediococcus may grow as well. Within the Leuconostoc genus, the species Ln. oenos is particularly adapted to grow in wines and this species is commonly used in commercial cultures as described above.

Recently, it has been suggested to change the designation *Leuconostoc oenos* to *Oenococcus oeni*. Accordingly, when the designation *Ln. oenos* is used herein, it is to be understood as also meaning *Oenococcus oeni*. Species of *Lactobacillus* which are of particular interest as malolactic starter culture organisms include *Lactobacillus casei, Lactobacillus brevis, Lactobacillus hilgardii* and *Lactobacillus plantarum*.

However, within a species of malolactically active bacteria there may exist differences between different isolates as to tolerance to one or more of the above-mentioned adverse conditions in wine. Accordingly, it may by applying appropriate methods be possible to select, within a species of malolactically active bacteria, isolates (strains) which are particularly tolerant to one or more of the adverse conditions. However, it is known in the art that when selecting a bacterial strain against one desired characteristic, such a strain will frequently be industrially less useful due to deficiencies as to other desired characteristics. E.g. may a strain selected on the basis of a high tolerance to acidic conditions be susceptible to moderate amounts of ethanol.

In a first step of the presently claimed method, a selection is carried out to obtain a strain of malolactically active bacteria, capable of starting malolactic fermentation in wine or fruit juice when added directly thereto at a concentration of less than $10^7$ CFUs per ml, the strain having at least one of the following characteristics:

(a) capable of decarboxylating malic acid in wine at a pH of 3.2 or lower,
(b) capable of decarboxylating malic acid in wine in the presence of 25 mg $SO_2$ per l or more,
(c) capable of decarboxylating malic acid in wine having an ethanol content of 10 vol % or higher,
(d) a survival rate of at least 80% when introduced into a wine having a pH of 3.2 or lower and containing at least 10 vol % ethanol,
(e) a survival rate of at least 50% when introduced into a wine having a pH of 3.2 or lower and containing at least 25 mg $SO_2$ per l and at least 12 vol % ethanol,
(f) resistant to attack by bacteriophages, or
(g) capable of retaining at least one of the characteristics (a) through (f) during propagation and concentration.

As used herein the term "survival rate" is defined as the percentage of CFU/ml in the wine after 2 days, calculated on the initial CFU/ml determined immediately after inoculation, the CFU/ml being determined in a non-selective medium.

When the selection criteria as those defined above have been determined, appropriate selection procedures known per se in the art can readily be chosen. Initially, a large number of strains of malolactically active bacteria are isolated from different types of wines and preferably from a range of viticultural regions. Such isolates may subsequently be tested individually according to each of the above selection criteria. However, such a conventional selection step is tedious. In accordance with the present invention a number of the isolates may more conveniently be combined and subjected to a first selection in a wine used as a growth medium in a turbidostat fermenter to obtain selection of strains which are capable of growing in a wine at a low pH and a high ethanol content.

When using such a turbidostat growth selection procedure, the mixture of isolates are inoculated into a fermenter and the biomass is kept constant by means of a turbidimeter. The culture is fed a nutrient-enriched wine with an increasing concentration of ethanol and a decreasing pH. When the pH level and the ethanol concentration is so high that no further bacterial growth is possible, a sample of the culture is drawn and representative strains of viable malolactically active bacteria are isolated and characterized.

In preferred embodiments of the above selection procedure, cultures of 5 to 50 strains such as e.g. 30 to 40 strains are inoculated into a fermenter such a 1 l fermenter containing a sterile filtered wine having initially a pH in the range of 3 to 4, such as in the range of 3.2 to 3.6 and an ethanol content which is in the range of 10 to 12% (v/v). In the present context, one example of a useful wine is a Riesling white wine having initially a pH of 3.4 and an ethanol content of 11.5%. The fermenter is preferably operated under constant stirring using a magnetic stirring at e.g. 200 rpm at a temperature in the range of 15 to 20° C. such as e.g. at about 18° C. for 4 to 6 weeks. During operation, the biomass in the fermenter is kept constant e.g. at an $OD_{600}$ of about 0.10 by means of a photometer which controls the addition of yeast extract enriched Riesling wine containing an increasing concentration of ethanol and a decreasing pH. After a period of 4 to 6 weeks of cultivation, the pH and the ethanol concentration in the fermenter reaches values where further growth of the bacteria is ceased, such as pH below 3.1 and ethanol concentrations in the range of 14–15% (v/v). At this point of time a sample is drawn and representative strains of viable acid and ethanol tolerant *Ln. oenos* are selected.

In a second selection step, such isolated acid and ethanol tolerant strains are tested in wines having different compositions for the characteristics as mentioned above.

In a subsequent third selection step, such selected strains are subjected to fermenter propagation under production conditions, e.g. as described in the following examples, in order to select strains which in addition to the above characteristics have an industrially feasible growth yield and which at the same time maintain the characteristics based on which they were selected. Typically a feasible growth yield before harvesting cells is at least about $1 \times 10^9$ CFU/ml of the propagation medium, such as at least about $2 \times 10^9$ CFU/ml. After concentrating the cells a yield of at least about $5 \times 10^{10}$ CFU/g of concentrate, such as at least about $1 \times 10^{11}$ CFU/g is preferably obtained. After freeze-drying a concentrate which contains at least about $1 \times 10^{11}$ CFU/g, such as at least about $1 \times 10^{12}$ CFU/g is typically obtained.

In this connection it has been found that the composition of the medium used in the above third selection step has a significant effect on the ability of the selected strains to retain their tolerance to the conditions in wine, in particular their ability to survive in a wine having a low pH when they are inoculated directly into such wine.

A typical conventional propagation medium for malolactically active *Ln. oenos* strains has a composition as that of the GJ-3 medium described in the following. This medium contains i.a. DL-malic acid which, however, has a considerable buffering capacity. The purpose of using a conventional propagation medium having a high buffering capacity is to maintain pH throughout the propagation at a relatively high level with the aims of obtaining a desired high biomass yield.

However, it has surprisingly been found that, when the malic acid is left out of the conventional propagation medium the ability of the propagated strains to survive when they are subsequently inoculated directly into a wine having a low pH and/or a high ethanol content, is better maintained as compared to that of the strain when it is propagated in the propagation medium containing malic acid. It was demonstrated that this effect on maintenance of survivability of selected strains is due to the resulting relatively lower pH occurring during propagation of the selected strains in such a medium. In particular, it was found that the ability of selected strains to survive and grow when inoculated into wine was significantly enhanced when the pH in the inoculum was in the range of 3.3 to 4.0. Examples of such a propagation medium without malic acid which is useful in this selection step include the GJ-4 medium and the GJ-5 medium as described in the following examples.

In a final selection step, the strains which pass the preceeding step are subjected to a down-stream process including at least one of the following steps: harvesting of cells from the culture medium, concentrating the cells, freezing of the concentrate or freeze-drying to obtain a malolactically active *Ln. oenos* strain according to the invention.

It will be understood that a selected strain should preferably have as many as possible of the above-defined characteristics (a) through (g). Accordingly, the selected strain is preferably one which has at least two of the characteristics, more preferably one having at least three of the characteristics and most preferably the strain is one which has all of the defined characteristics. In particular, the selected strain should in addition to other advantageous characteristics have a high rate of survival under the conditions as defined above. A high survival rate makes it possible to have the MLF started at the low CFU concentrations as defined above and allow the high proportion of surviving cells to enter the active growth phase and become malolactically active essentially momentaneously or within a short period of time such as within 1–3 days, thereby obtaining the malolactically fermented wine or fruit juice within the short periods of time as defined herein. It may be observed with cultures having a low survival rate and applied in high concentrations that although an initial conversion of malic acid takes place due to the release of malolactically active enzymes from the killed cells, the active growth phase is entered only after a prolonged lag phase of 5–10 days and accordingly, such cultures will not be suitable for obtaining a rapid MLF and particularly, these cultures will not result in a conversion of high amounts of malic acid within an industrially acceptable period of time, such as it is obtained with the present selected strains.

In accordance with the invention, a suitable malolactically active bacterial strain is one selected from a species belonging to the genera of *Leuconostoc, Lactobacillus* and *Pediococcus*. When the strain is selected from a species of the *Leuconostoc* genus, the species is preferably *Ln. oenos* such as a strain which is selected from the group consisting of DSM 7008, DSM 7009, DSM 7010, DSM 7011, DSM 7012, DSM 7013, DSM 7014 and DSM 7015. These 8 strains were deposited on 26 Mar., 1992 with Deutsche Sammlung von Mikroorganismen und Zellkulturen GmbH (German Collection of Microorganisms and Cell Cultures), Braunschweig, Germany.

In one aspect of the invention there is provided a concentrate of the thus selected malolactically active strain. The concentrate is preferably one in which the number of colony forming units is in the range of $10^9$ to $10^{13}$ per g. In more preferred embodiments, the concentrate has a number of colony forming units which is in the range of $10^{10}$ to $10^{12}$ per g.

As an initial step in the obtainment of the concentrate, a chosen selected strain is propagated using equipment which is well-known in the art. Such a propagation includes the step of propagating the strain in a suitable fermenter vessel containing a suitable growth medium containing sufficient amounts of nutrients required for economically feasible growth yield of the particular strain. In accordance with the invention, a suitable growth medium for propagation of malolactically active bacteria contains as the major ingredient grape juice to which may be added yeast concentrate or extract, a surface active substance such as Tween™ 80, a manganese salt and water. One example of a suitable production medium is the GJ-5 medium as described in the following.

It was found that although a relatively low initial pH in the production medium such as a pH in the range of 3.5 to 4.0 is important for retaining the ability of the selected strains to survive the direct inoculation into wine, such a low pH may be less suitable for production purposes, since it results in a lowering of the biomass cell yield. Accordingly, it may be advantageous to use a production medium having a pH which is still at so low a level that an enhancing effect on viability of the selected strains is obtained when they are directly inoculated into wine, but which is not so low that significant decrease in the biomass yield occurs. Thus, it was found that an initial pH in the medium in the range of 3.5 to 4.5 such as in the range of 4.0 to 4.3 is suitable for the purpose of producing the *Ln. oenos* strains according to the invention.

In preferred embodiments of the above production method the production medium has a composition permitting propagation to occur at a pH being at the most 4.0 for at least 2 hours. A production medium permitting the propagation to occur at a pH being at the most 4 for at least 6 hours such as for at least 10 hours is preferred. Propagation periods of 30 hours or more at a pH of at the most 4 has been found to significantly enhance survival and growth in wine of the selected strains.

In accordance with the claimed method the propagation is performed at a temperature in the range of 25 to 35° C., such as 28 to 32° C., preferably at about 30° C.

Subsequent to the above propagation step, the cell biomass is harvested e.g. by centrifugation whereby a concentrate of cells is obtained in the form of a slurry or a cell paste. Alternatively, the concentrate of cells may be obtained by a filtration process. Although such a fresh cell paste may be used to inoculate a wine or fruit juice, the bacterial concentrate is more conveniently provided in the form of a preserved concentrate, since the viability of cells in a cell paste concentrate will decrease rapidly and furthermore, a fresh cell paste will be prone to growth of contaminating microorganisms. In accordance with the invention, a concentrate may be preserved by freezing e.g. by dripping the paste into liquid nitrogen or by introducing the cell paste into a suitable freezing apparatus. In order to retain the viability of cells during freezing, the paste may be mixed with suitable cryoprotectants such as gelatine, prior to freezing. In a preferred embodiment of the invention, the concentrate is provided as a freeze-dried concentrate which is typically prepared by subjecting a frozen concentrate to a conventional freeze-drying process.

In the claimed method of converting malic acid in wine or fruit juice to lactic acid, a concentrate of the selected malolactically active strain is inoculated directly into the malic acid-containing wine or fruit juice. In the present context, the term "inoculated directly" is used to describe that the concentrate as defined herein is added to the wine or fruit juice without any prior activation and/or adaptation step. It will be understood that the terms "activation" and "adaptation" does not cover a brief step of rehydrating and/or suspending the concentrate in a liquid prior to inoculation, with the sole purpose of facilitating the subsequent homogeneous distribution of the Ln. oenos cells in the wine. If such a rehydration and/or suspension step is used, it is typically of a length up till 60 minutes, such as up till 30 minutes, e.g. 5–15 minutes. As it has been explained above, the known commercial malolactic starter cultures for post-alcoholic MLF all require that they are subjected to an adaptation step including an activation step and optionally (if they are in a freeze-dried state) an initial rehydration step, prior to inoculation. If such known cultures are inoculated directly, the viability of the cells is typically reduced by a factor of 100 to 1000.

The concentrate is added to the wine or the fruit juice in an amount which results in the introduction of a number of bacteria, calculated on a CFU basis which typically is in the range of $10^5$ to $10^8$ per ml but preferably in the range of $10^5$ to $10^7$ per ml. The preferred inoculation rate depends on several factors including the amount of malic acid to be converted, the desired period for obtaining the malolactically fermented wine or fruit juice and the temperature conditions. A typical preferred inoculation rate will be in the range of $10^6$ to $5 \times 10^7$ CFUs per ml and a more preferred range may be $5 \times 10^6$ to $1 \times 10^7$ CFUs per ml.

In a final step of the method of converting malic acid into lactic acid as claimed herein, the malic acid is converted to lactic acid while keeping the inoculated wine or fruit juice under conditions which will allow the conversion to take place. In particular, it is required to keep the wine or the fruit juice at a temperature where the inoculated culture is malolactically active. The majority of malolactic bacteria will be active at temperatures in the range of about 12 to about 25° C. A typical temperature for storing wine undergoing malolactic fermentation will be in the range of about 15 to 22° C.

As mentioned above, the content of malic acid in a wine may vary, in particular according to the climatic conditions of the viticultural region. Typically, the malic acid content will be in the range of 2 to 10 g per l. In specific embodiments of the invention, the wine or fruit juice to be malolactically fermented as defined herein is one having a malic acid content of at least 4 g per l, such as at least 5.5 g per l. In accordance with the invention, a malolactically fermented wine or fruit juice containing less than 0.5 g malic acid per l should preferably be obtained from such a wine or fruit juice within a period of time which is at the most 15 days. In more preferred embodiments, the period of time is at the most 12 days and in still more preferred embodiments it is at the most 10 days such as at the most 8 days.

In particularly preferred embodiments of the present invention, the obtained malolactically fermented wine or fruit juice has a malic acid content which is at the most 0.1 g per l.

As mentioned above, the present invention relates in further aspects to a strain of a malolactically active bacterium which has been selected according to the methods and selection criteria as defined above and to a concentrate of such a selected strain as also defined above.

Finally, the present invention provides a malolactic starter culture composition comprising the concentrate as defined herein and at least one further ingredient selected from cryoprotectants, including as an example gelatine, bacterial nutrients and bulking agents.

Conveniently, the claimed composition is preserved to obtain a commercial product which has a suitable shelf-life when stored and distributed appropriately. Accordingly, the composition is suitably a frozen or a freeze-dried composition which has been prepared by subjecting a mixture of the bacterial concentrate and the further ingredient(s) to a freezing and/or freeze-drying process essentially in accordance with the above-mentioned processes used for the claimed concentrate.

Preferably, the composition is one having a content of colony forming units which is in the range of $10^9$ to $10^{13}$ per g, such as in the range of $10^{11}$ to $10^{12}$ per g.

In useful embodiments of the invention, the composition is one which when it is inoculated directly into a wine or a fruit juice containing at least 4 g of malic acid per l such as at least 5.5 g per l at a concentration of CFUs which is in the range of $5 \times 10^6$ to $5 \times 10^7$ per ml, results in a malolactically fermented wine containing at the most 0.5 g malic acid per l within a period of time which is at the most 15 days, preferably at the most 12 days and more preferably at the most 10 days such as at the most 8 days.

It may be advantageous to provide the claimed composition as a composition comprising a multiplicity of the hereindefined selected strains of malolactically active bacteria. Accordingly, in one embodiment the composition comprises such a multiplicity.

DESCRIPTION OF DRAWINGS

The invention is further explained below with reference to the drawings in which.

EXAMPLE 1

Survival and Grown of *Ln. oenos* in an Experimental Wine

An experimental wine was prepared by yeasting a sterile Reisling grape juice originating from Germany, without the addition of sulphite. After completion of the alcoholic fermentation, the wine was sterile filtered and the resulting wine had the following composition:

| | |
|---|---|
| Ethanol | 11.5 vol % |
| Malic acid | 3.9 g/l |
| Residual sugar | 3.5 g/l |
| pH | 3.15 |

A culture of *Ln. oenos* strain DSM 7008 (LOD 890004) was prepared as described below, and the sterile wine was inoculated with (1) cells of the strain directly from the fermentate (i.e. the growth medium containing an outgrown culture of the strain), (2) a cell concentrate after centrifugation, (3) a cell concentrate to which cryoprotective agents had been added or (4) a freeze-dried composition of a cell concentrate with added cryoprotectants, respectively. The numbers of CFUs which were inoculated by the four mentioned forms of the strain varied between $3 \times 10^6$ and $7 \times 10^6$ per ml of the experimental wine.

The survival of the added bacteria in the wine kept at 20° C. was monitored over 3 days, samples being collected on day 2 and 3 and the number of CFUs herein being determined according to standard methods for determining viable counts of *Ln. oenos*.

Figure 1:
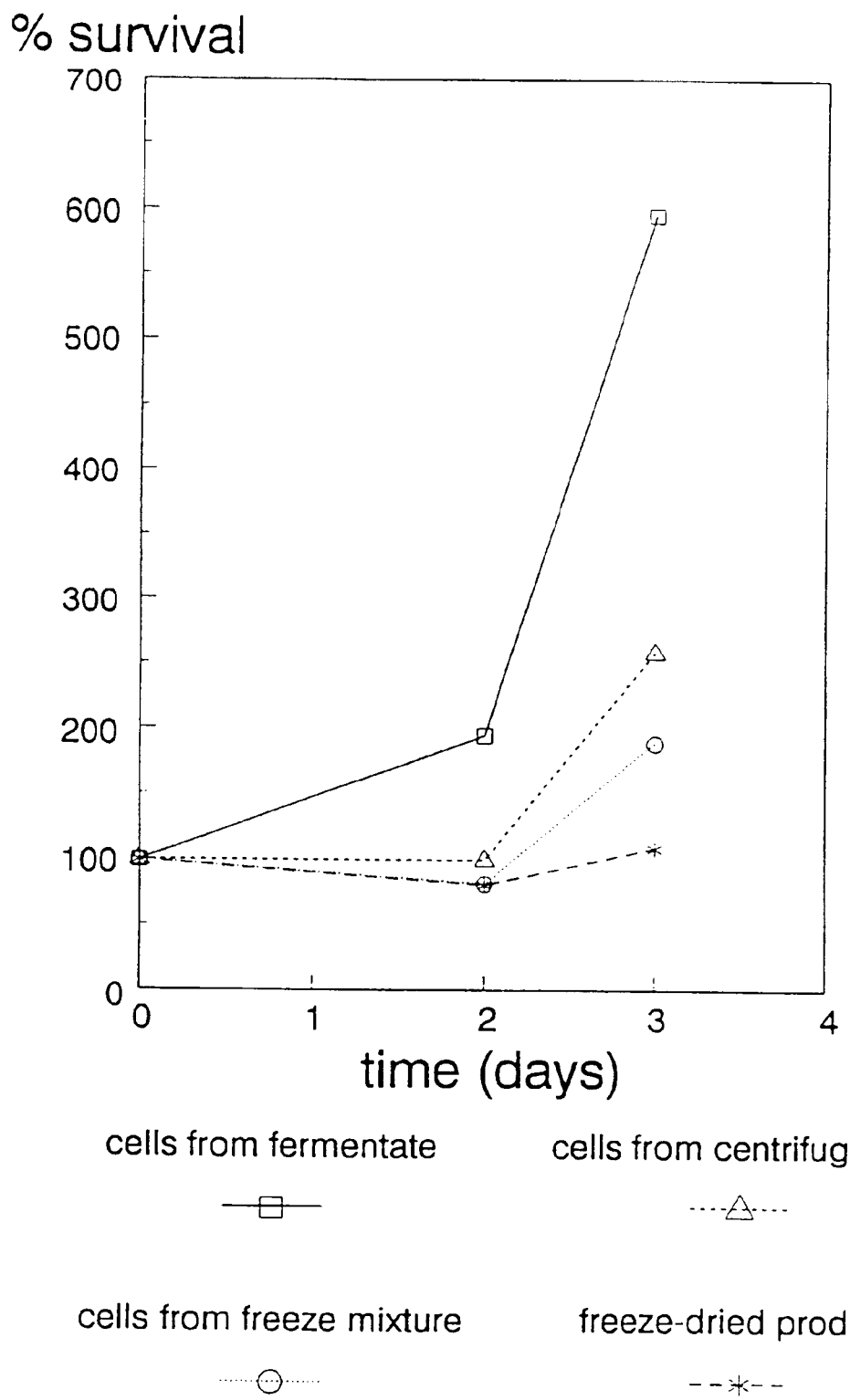
FIG. 1 shows the survival and growth (CFU/ml) of Ln. oenos strain DSM 7008 as fresh culture (fermentate) and as processed concentrates after direct inoculation into wine made from Riesling grape juice (11.5 vol % ethanol, 0 mg $SO_2$ per l, pH 3.15) of $3 \times 10^6$ to $7 \times 10^6$ per ml.
Figure 2A:
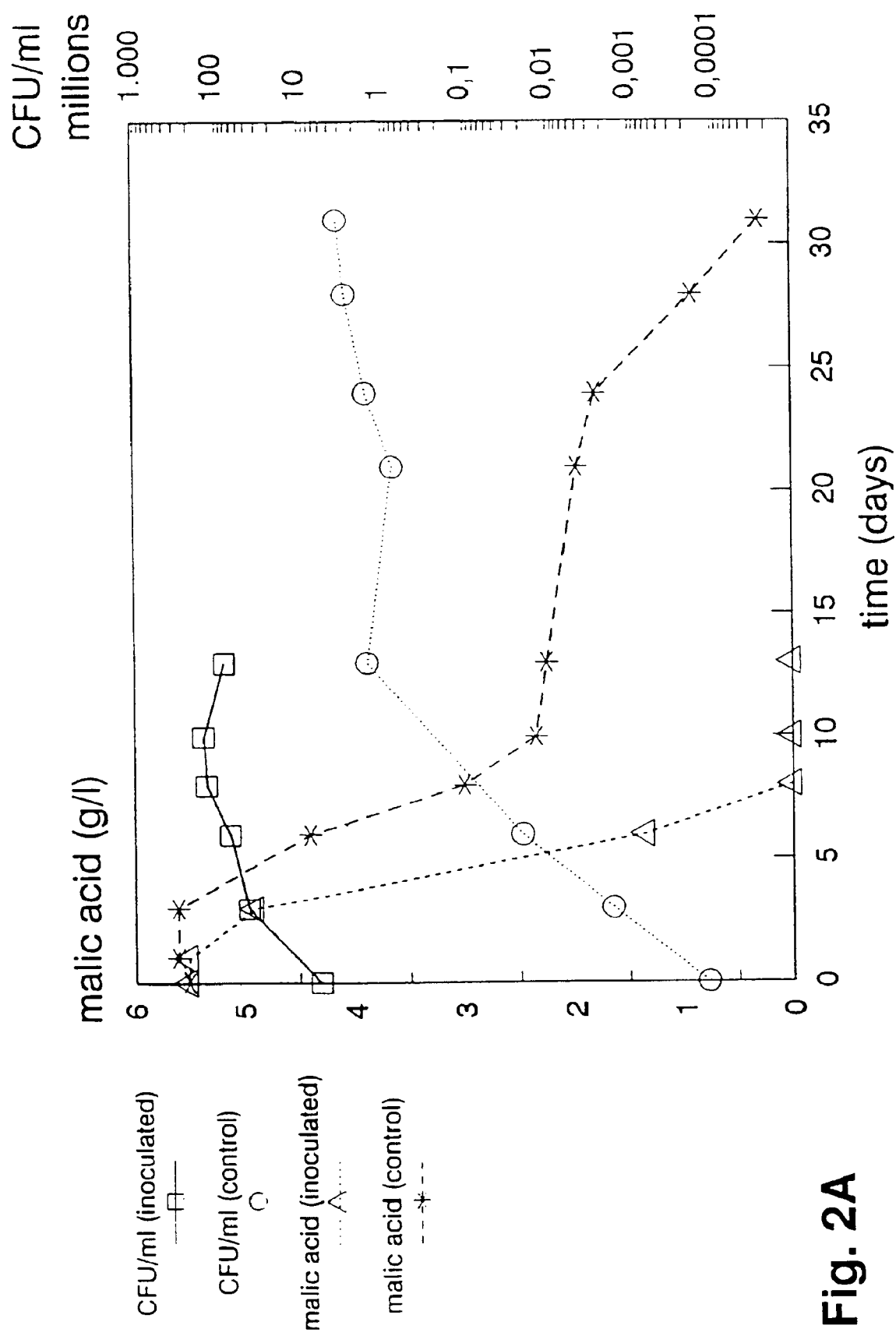
FIG. 2A shows the conversion of malic acid and CFU/ml of malolactically active bacteria in Chénin white wine (10.5 vol % ethanol, 16 mg $SO_2$/ml, pH 3.5, 0.004 g/l of glucose and 0.003 g/l of fructose) kept at 18° C. in 5 l jars inoculated with a freeze-dried composition of Ln. oenos strain DSM 7008, and in the same wine without inoculation.
Figure 2B:
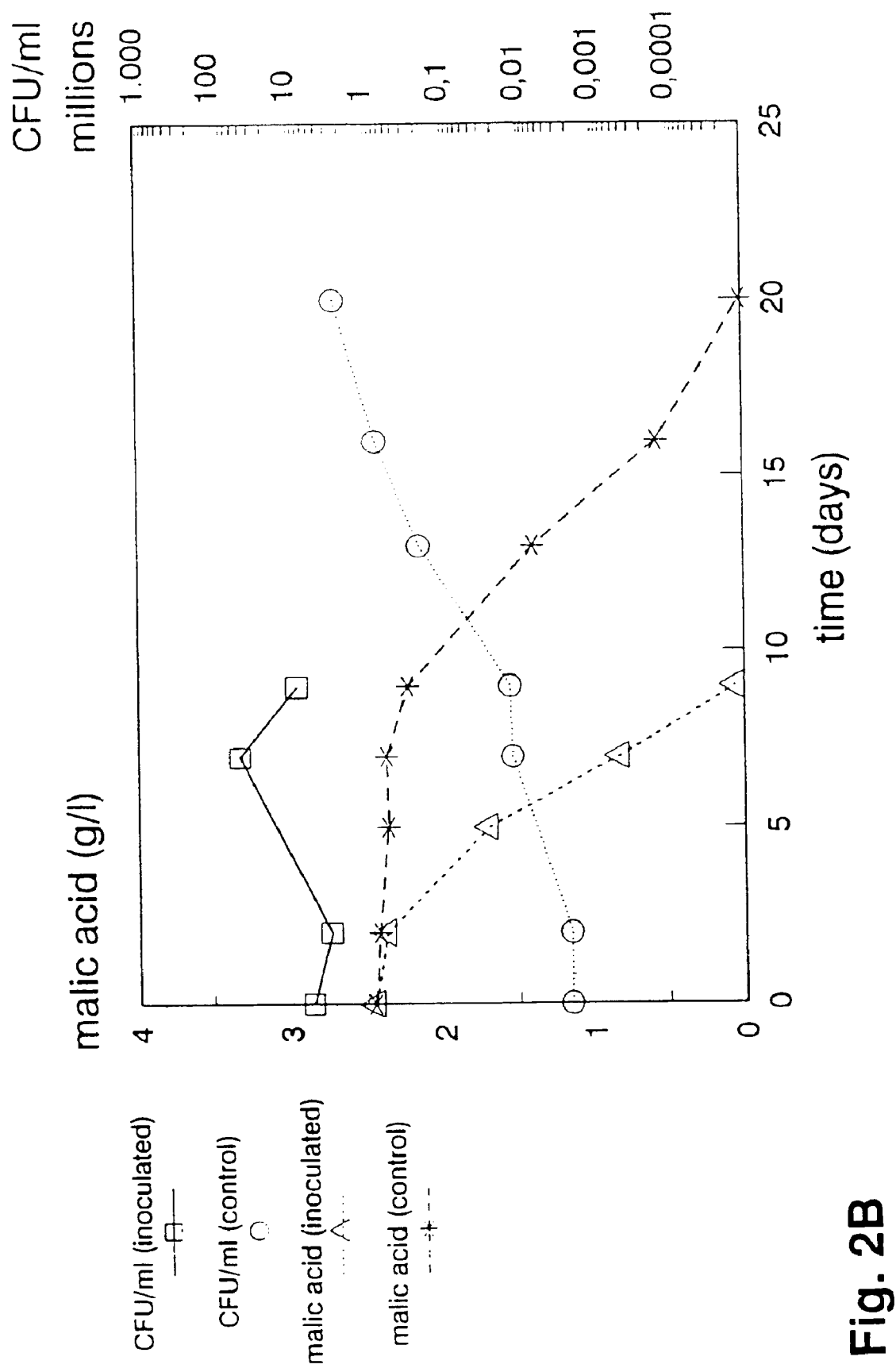
FIG. 2B shows the conversion of malic acid and CFU/ml of malolactically active bacteria in Cabernet Sauvignon red wine (11.0 vol % ethanol, 0 mg $SO_2$/ml, pH 3.6, 0.11 g/l of glucose and 0.07 g/l of fructose) kept at 20° C. in 5 l jars inoculated with a freeze-dried composition of *Ln. oenos* strain DSM 7008, and in the same wine without inoculation.
Figure 2C:
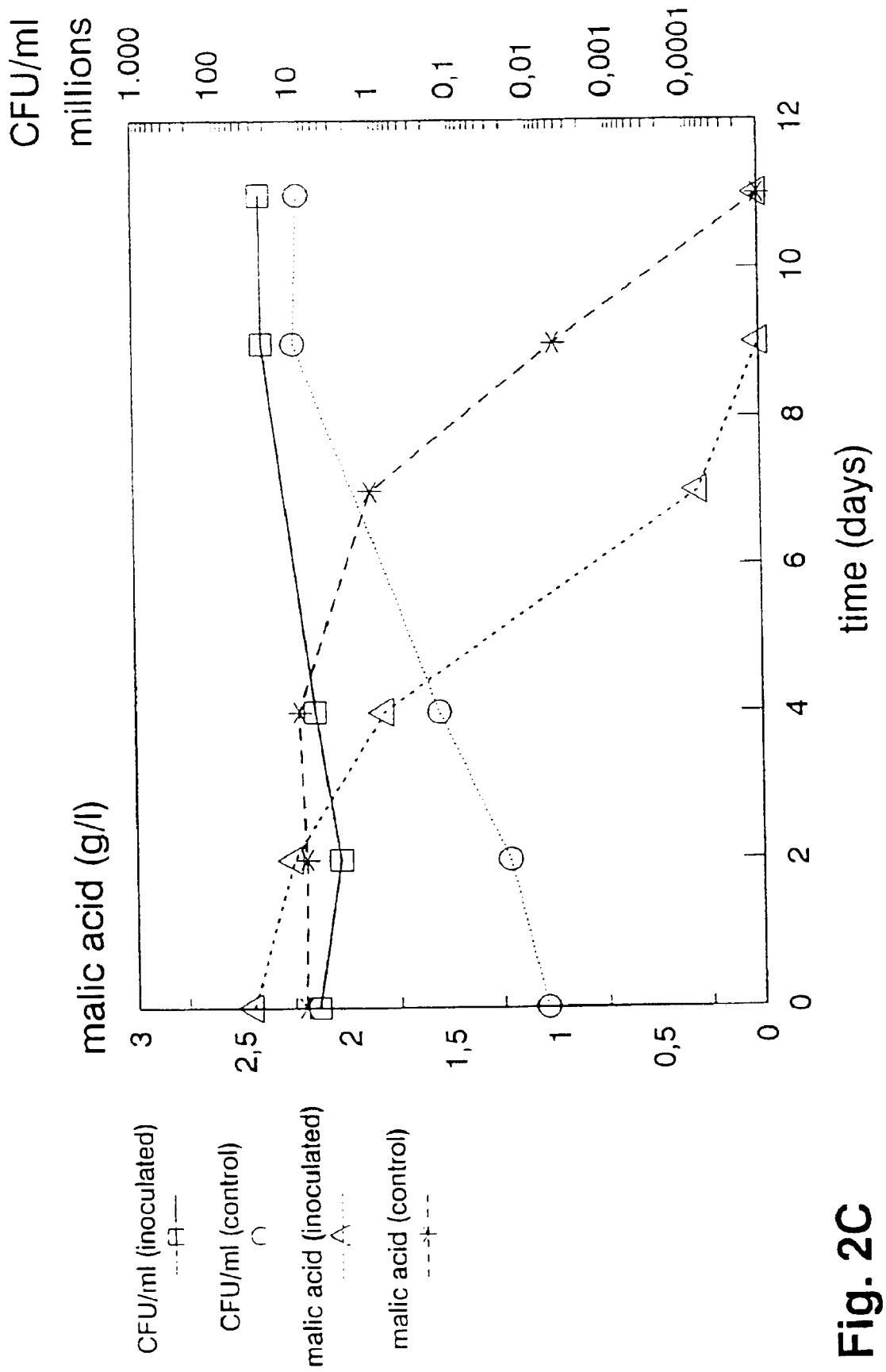
FIG. 2C shows the conversion of malic acid and CFU/ml of malolactically active bacteria in Cabernet Sauvignon red wine (11.3 vol % ethanol, 0 mg $SO_2$/ml, pH 3.6, 0.11 g/l of glucose and 0.07 g/l of fructose) kept at 21° C. in 10.000 l insulated tanks inoculated with a freeze-dried composition of *Ln. oenos* strain DSM 7008, and in the same wine without inoculation.
Figure 2D:
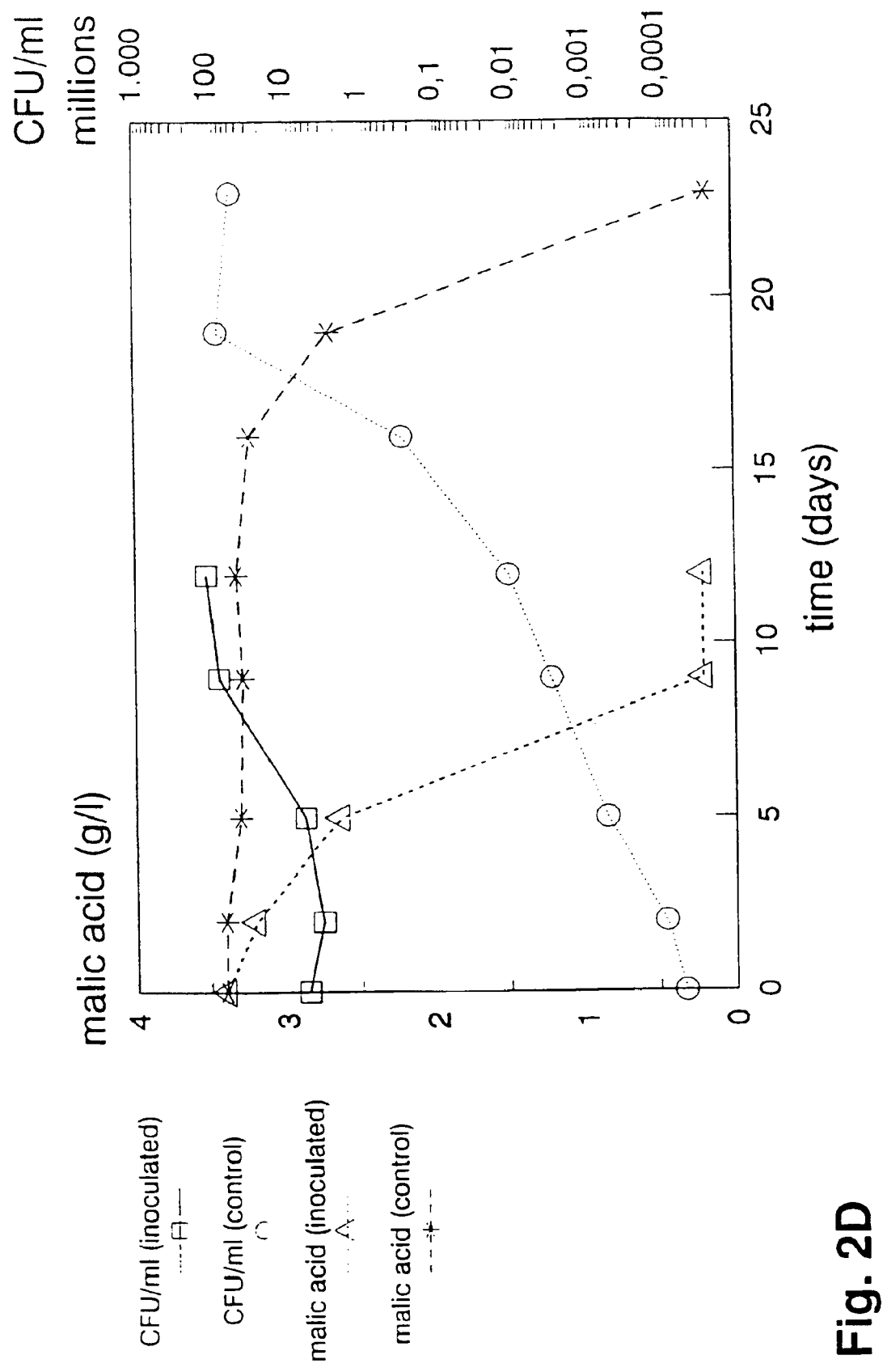
FIG. 2D shows the conversion of malic acid and CFU/ml of malolactically active bacteria in Cabernet Sauvignon red wine (11.8 vol % ethanol, 5 mg $SO_2$/ml, pH 3.5, 0.3 g/l of glucose and 0.45 g/l of fructose) kept at 20° C. in 5 l jars inoculated with a freeze-dried composition of *Ln. oenos* strain DSM 7008, and in the same wine without inoculation.
Figure 2E:
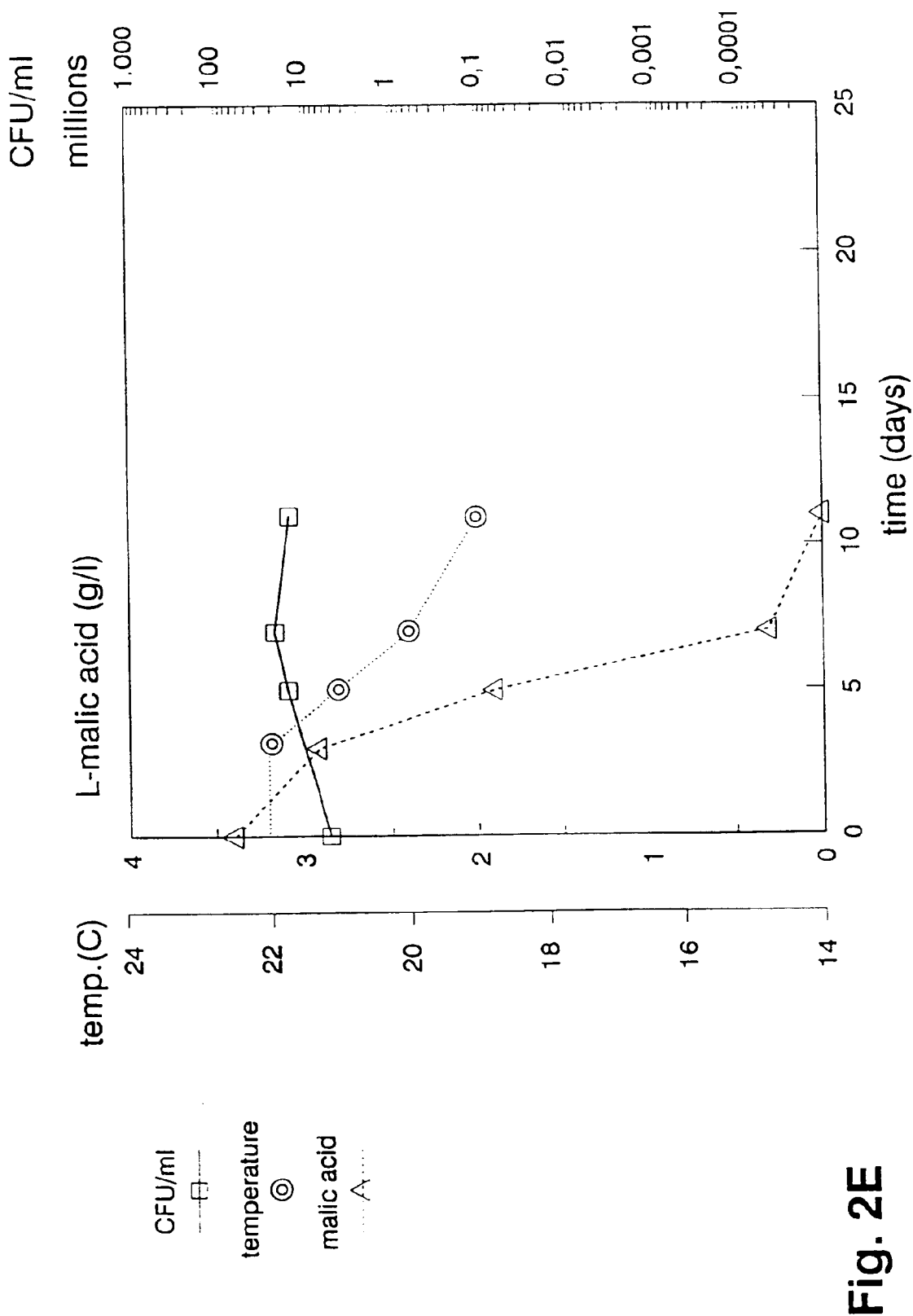
FIG. 2E shows the conversion of malic acid and CFU/ml of malolactically active bacteria in Cabernet Sauvignon red wine (11.8 vol % ethanol, 5 mg $SO_2$/ml, pH 3.5, 0.3 g/l of glucose and 0.45 g/l of fructose) kept at 20° C. in 5 l jars inoculated with a freeze-dried composition of *Ln. oenos* strain DSM 7008, and in the same wine without inoculation.
Figure 2F:
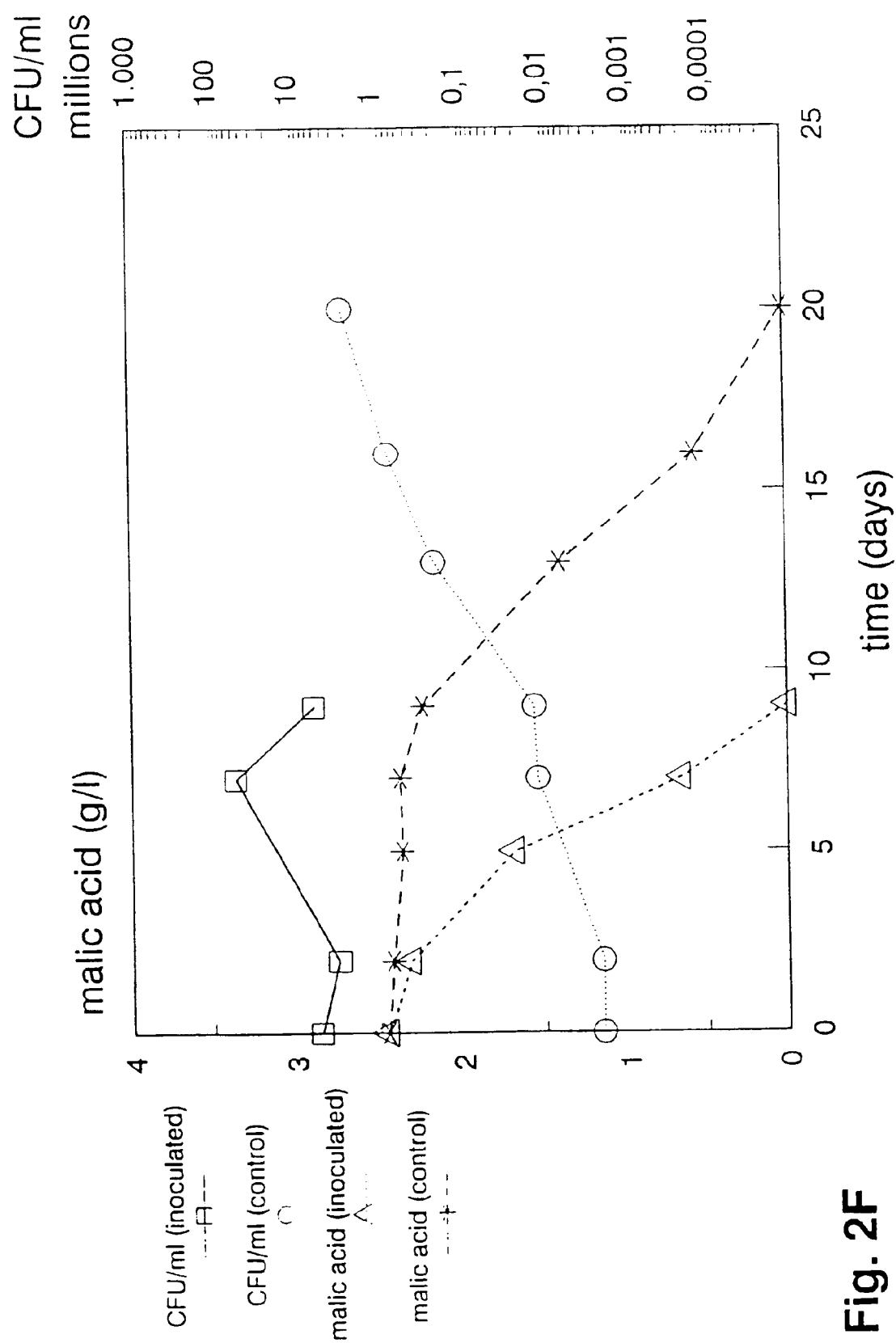
FIG. 2F shows the conversion of malic acid and CFU/ml of malolactically active bacteria in Cabernet Sauvignon red wine (11.0 vol % ethanol, 0 mg $SO_2$/ml, pH 3.6, 0.11 g/l of glucose and 0.07 g/l of fructose) kept at 20° C. in 5 l jars inoculated with a freeze-dried composition of *Ln. oenos* strain DSM 7015, and in the same wine without inoculation.
Figure 2G:
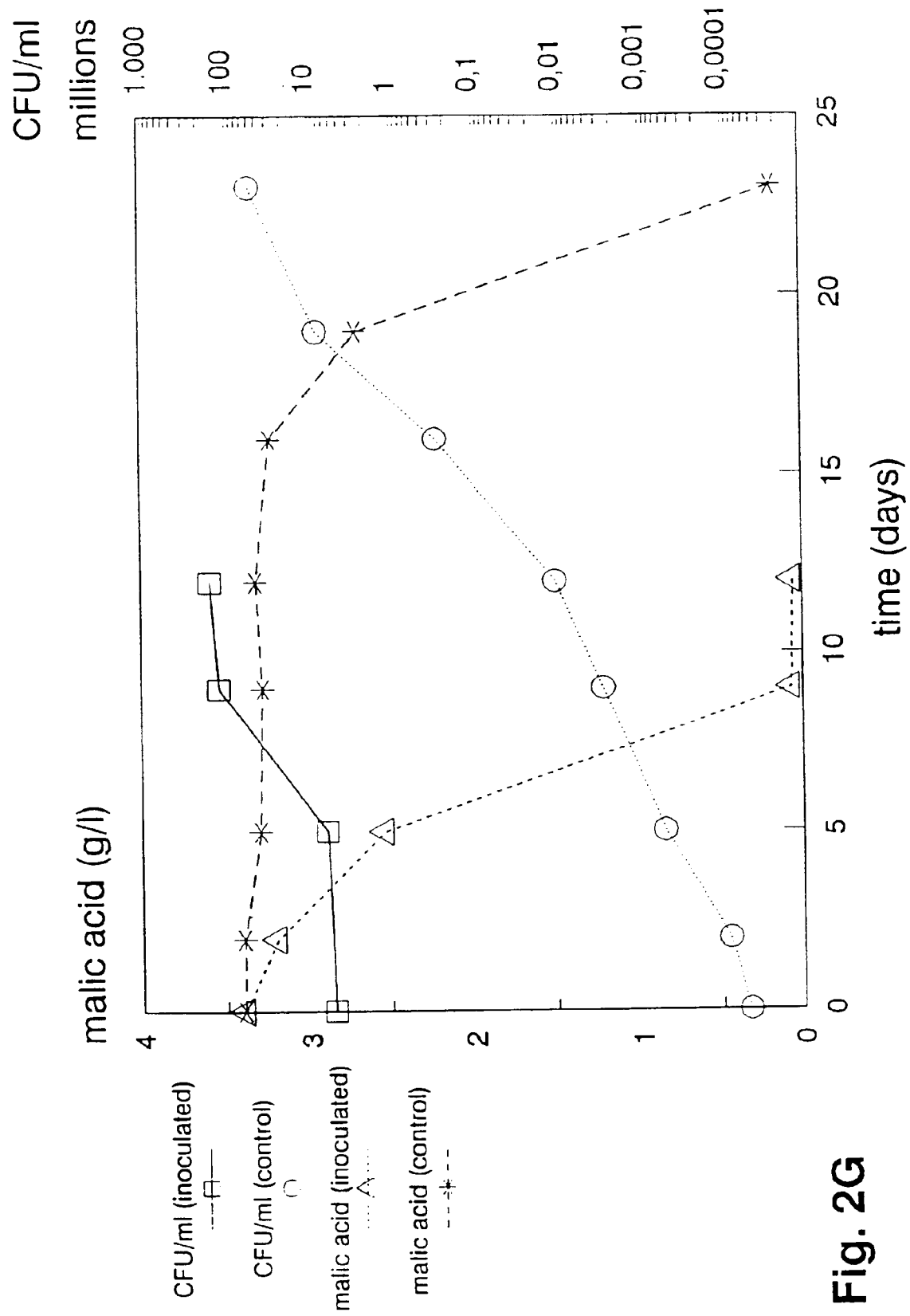
FIG. 2G shows the conversion of malic acid and CFU/ml of malolactically active bacteria in Cabernet Sauvignon red wine (11.8 vol % ethanol, 5 mg $SO_2$/ml, pH 3.5, 0.3 g/l of glucose and 0.45 g/l of fructose) kept at 20° C. in 5 l jars inoculated with a freeze-dried composition of *Ln. oenos* strain DSM 7015, and in the same wine without inoculation.
Figure 2H:
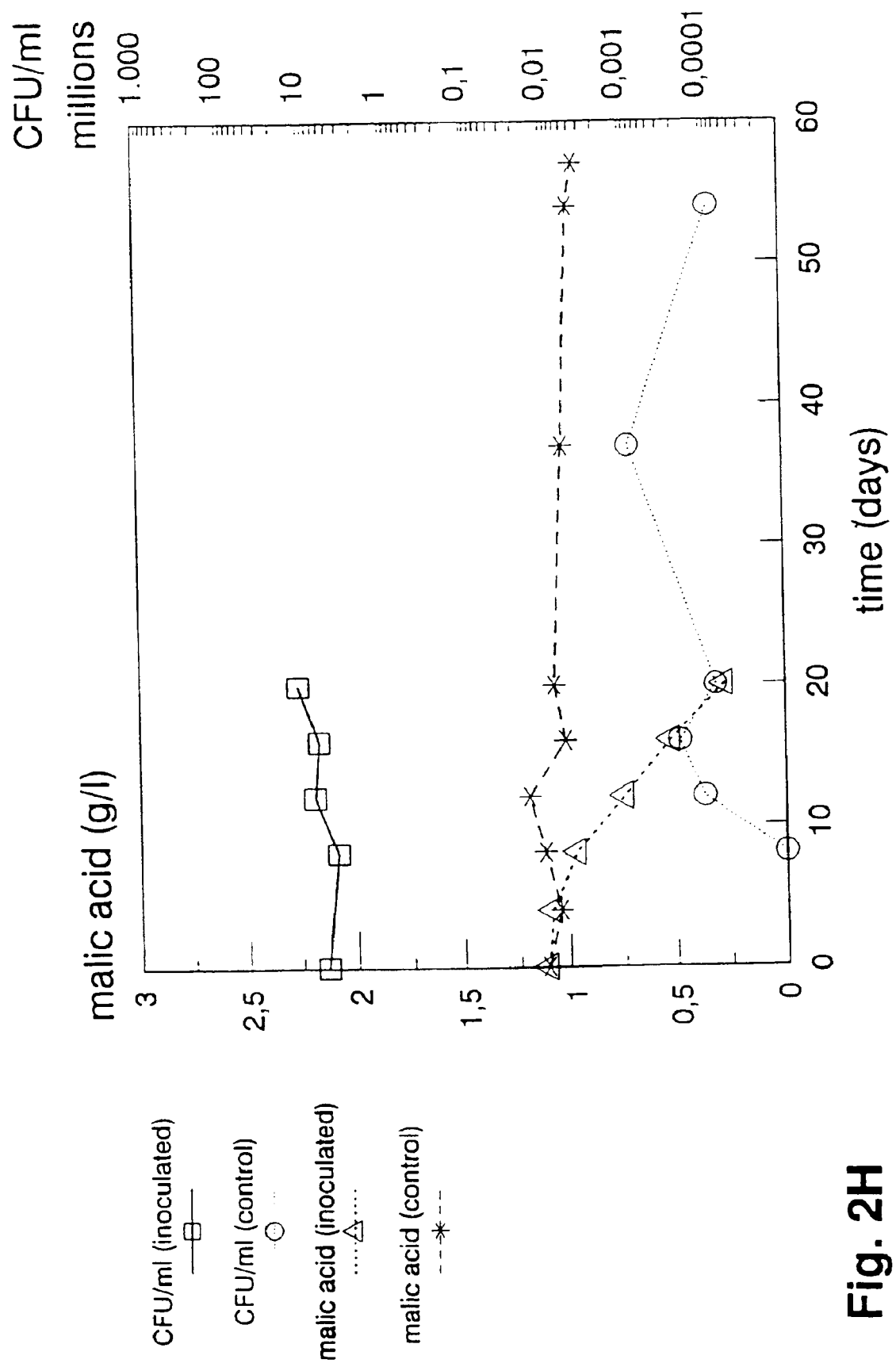
FIG. 2H shows the conversion of malic acid and CFU/ml of malolactically active bacteria in Cabernet Franc red wine (13.0 vol % ethanol, 2 mg $SO_2$/ml, pH 3.4) kept at 20° C. in 5 l jars inoculated with a freeze-dried composition of *Ln. oenos* strain DSM 7008, and in the same wine without inoculation.
Figure 2I:
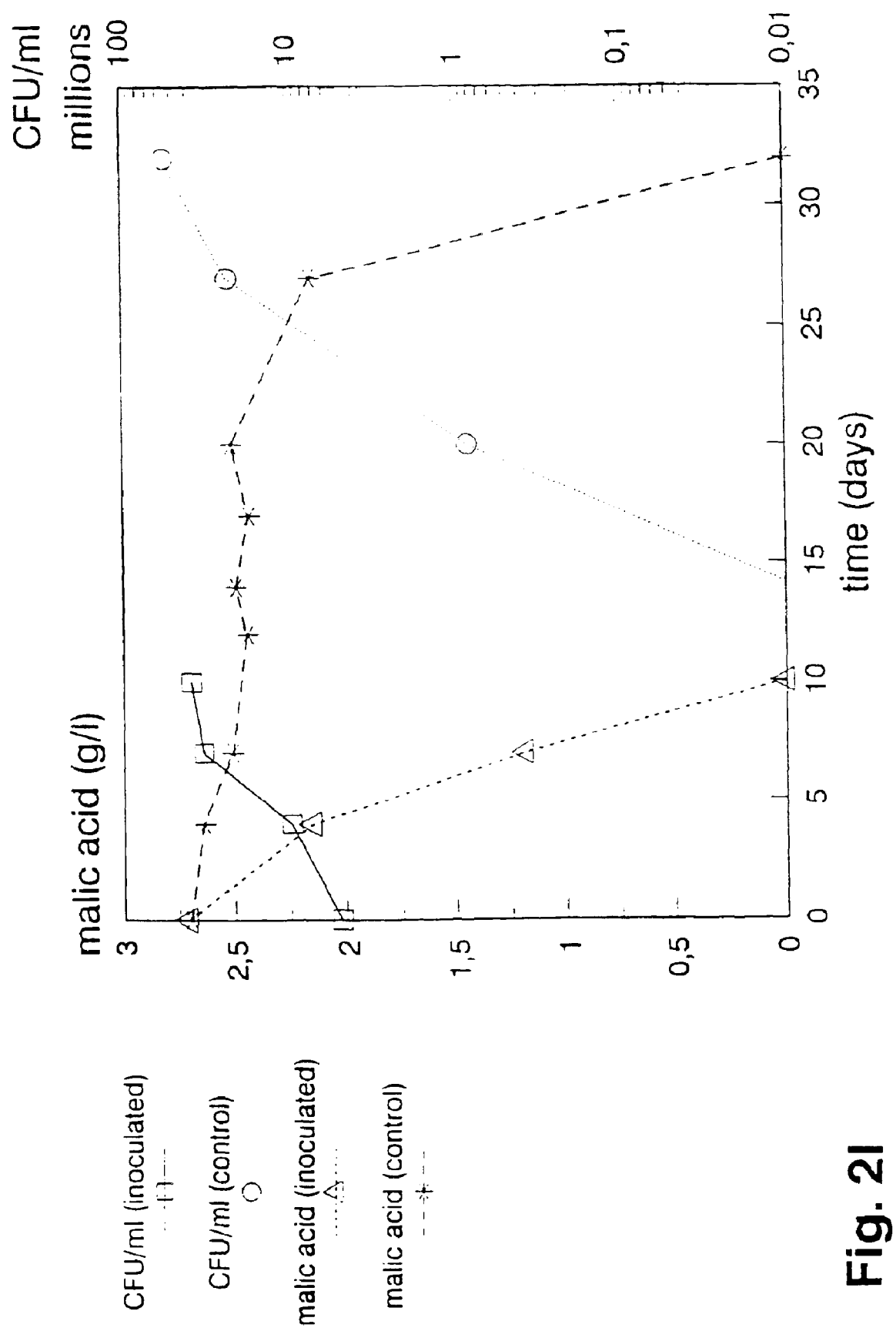
FIG. 2I shows the conversion of malic acid and CFU/ml of malolactically active bacteria in Sémillon white wine (12.2 vol % ethanol, 26 mg $SO_2$/ml, pH 3.2) kept at 19° C. in 5 l jars inoculated with a freeze-dried composition of *Ln. oenos* strain, DSM 7008, and in the same wine without inoculation.

The results of this experiment are shown in FIG. 1 from which it appears that the bacteria when added in the form of a fermentate multiplied during the keeping time, with a factor of about 6. Bacteria added in the form of processed inocula showed a survival rate after 2 days which was in the range of 80% to 100% and during the next day the numbers of CFUs of these inocula increased by 10% to 60% relative to the initial numbers.

EXAMPLE 2

Induction of Malolactic Fermentation in Red Wines and White Wines by Direct Inoculation with *Ln. oenos*—containing Compositions The malolactic effect of freeze-dried compositions of two strains of *Ln. oenos*, DSM 7008 and DSM 7015 were tested by direct inoculation into different wines. The study was carried out by inoculating wines in 5 l jars and in industrial scale by inoculating wines contained in 5.000 to 10.000 l tanks. The inoculum level was about $5 \times 10^6$ per ml of wine.

The study comprised the following experiments:
1. Inoculation with strain DSM 7008 of Chénin white wine from the Loire region contained in 5 l jars.
2. Inoculation with strains DSM 7008 and DSM 7015 of Cabernet Sauvignon red wine from Graves in the Bordeaux region, kept in 5 l jars and additionally with DSM 7008 in a 10.000 l tank.
3. Inoculation with strains DSM 7008 and DSM 7015 of Cabernet Sauvignon red wine from Premières Côtes de Bordeaux contained in 5 l jars and additionally with strain DSM 7008 in a 5.000 l tank. This wine had a content of ethanol of 11.8 vol % and a $SO_2$ content of 5 mg per l and a pH of 3.5.
4. Inoculation with strain DSM 7008 of Cabernet-Franc red wine from Premiéres Côtes de Bordeaux, kept in 5 l jars.
5. Inoculation with strain DSM 7008 of Semillon white wine from Côteaux de Montravel in the Bordeaux region, kept in 5 l jars.

The tested wines had an initial content of malic acid in the range of 3 to 5.5 g per l, and the content of $SO_2$ was in the range of 0 to 26 mg per l. In all of the inoculated wines the malolactic fermentation occurred at a rate which resulted in a substantially complete disappearance of malic acid within 8 to 20 days. The survival rate the of inoculated bacteria was 90 to 100% in the test wines and in most wines an increase of CFUs up till about $10^8$ per ml occurred during the malolactic fermentation period.

EXAMPLE 3

The Effect of Propagation Conditions on the Viability of Ln. oenos Used for Inoculation into an Experimental Wine 3.1. Isolation of Test Strains Cultures of 50 strains isolated from Spanish wines were inoculated into a 1 l fermenter containing a sterile filtered wine having initially a pH of 3.5 and an ethanol content of 11.5% (v/v). The fermenter was operated under constant stirring using a magnetic stirring at 200 rpm at a temperature of 18° C. The biomass in the fermenter was kept constant at an $OD_{600}$ of about 0.10 by means of a photometer which controlled the addition of an experimental wine, described in Example 1. For this purpose the experimental wine was enriched with 0.5 g yeast extract (Oxoid) per l and the ethanol concentration and the pH of the wine were adjusted with 96% (v/v) ethanol and 2 N HCl/NaOH, respectively, to stepwise decrease the pH. The turbidostate was supplied with a total of 16 l of yeast enriched experimental wine in 4 sequential batches with the following pH and ethanol concentrations:
Batch 1: pH 3.40 and 11.5% (v/v) ethanol (about 10.5 days)
Batch 2: pH 3.20 and 13.0% (v/v) ethanol (about 10.5 days)
Batch 3: pH 3.10 and 14.0% (v/v) ethanol (about 10.5 days)
Batch 4: pH 3.00 and 14.0% (v/v) ethanol (about 10.5 days)

After 6 weeks of cultivation, the pH and the ethanol concentration in the fermenter reached values of 3.1 and 14% (v/v), respectively and the cultivation was stopped. Samples were subsequently drawn and 6 strains of viable acid and ethanol tolerant Ln. oenos, LOD 89001, LOD 89002, LOD 89003, LOD 89004 (DSM 7008), LOD 89005 and LOD 89006 were isolated on MRS (deMann, Rogosa and Sharpe) agar. Using the same procedure, Ln. oenos strains DSM 7009, 7010, 7011, 7012, 7013, 7014, and 7015 were also isolated.

The above six LOD strains of Ln. oenos were propagated at 25° C. for 3 days in a conventional growth medium designated GJ-3 having the following composition:

| | |
|---|---|
| Grape juice concentrate | 70.0 g |
| Yeast paste | 10.0 g |
| DL-malic acid | 3.0 g |
| $(NH_4)_2PO_4$ | 1.0 g |
| Tween 80 | 0.5 g |
| $MnSO_4H_2O$ | 0.1 g |
| Tap water | 900.0 g |
| Vitamin mixture | 1 ml |

The pH was adjusted to 5.0.

The outgrown cultures were inoculated directly into the experimental wine described in Example 1. The strains were inoculated at a concentration of 1 ml per 1000 ml wine which was then incubated at 22° C. Samples for counting of colony forming units per ml (CFU/ml) were collected immediately after inoculation and after 1, 2, 5, 10 and 20 days, receptively. The method of counting was pour plating in MRS agar with incubation at 30° C. for 6 days.

The results which are summarized in Table 3.1 below showed that there was a rapid decline in viability. After 10 days only one strain had survived (LOD 89001) and after 20 days no colony forming units could be detected for any of the selected strains.

TABLE 3.1

CFU/ml in wine inoculated directly with Ln. oenos strains cultivated in GJ-3 medium, initial pH 5.0

| | Strains | | | | | |
|---|---|---|---|---|---|---|
| days | LOD 89001 | LOD 89002 | LOD 89003 | LOD 89004 | LOD 89005 | LOD 89006 |
| 0 | $2.6 \times 10^6$ | $2.7 \times 10^6$ | $5.0 \times 10^5$ | $1.3 \times 10^6$ | $2.6 \times 10^4$ | $8.9 \times 10^3$ |
| 1 | $8.1 \times 10^4$ | $1.2 \times 10^4$ | $1.0 \times 10^3$ | $5.0 \times 10^3$ | $2.0 \times 10^3$ | <1000 |
| 2 | $4.0 \times 10^4$ | $4.0 \times 10^3$ | <1000 | $2.0 \times 10^3$ | <1000 | <1000 |
| 5 | $2.6 \times 10^4$ | <1000 | <1000 | $2.0 \times 10^3$ | <1000 | <1000 |
| 10 | $1.1 \times 10^4$ | <1000 | <1000 | <1000 | <1000 | <1000 |
| 20 | <100 | <100 | <100 | <100 | <100 | <100 |

It was concluded from the above experiments that using the GJ-3 medium as a propagation medium generally resulted in a poor survival in wine of the test strains.

In an attempt to possibly improve the survival of the strains when inoculated into the experimental wine a modified propagation medium was developed, corresponding in all respects to GJ-3 medium, except that it did not contain malic acid. This modified medium was designated GJ-4 medium.

An experiment essentially similar to that with the GJ-3 medium-propagated strains was carried out using the GJ-4 medium.

Table 3.2 below summarizes the results of the colony counts. It appears that the survival in the wine of the tested strains propagated in GJ-4 medium was improved significantly as compared to the survival which was obtained with the same strains propagated in GJ-3.

TABLE 3.2

CFU/ml in wine inoculated directly with strains of
*Ln. oenos* cultivated in GJ-4 medium, initial pH 5.0

| | Strains | | | | | |
|---|---|---|---|---|---|---|
| days | LOD 89001 | LOD 89002 | LOD 89003 | LOD 89004 | LOD 89005 | LOD 89006 |
| 0 | $2.1 \times 10^6$ | $2.4 \times 10^6$ | $1.2 \times 10^6$ | $2.5 \times 10^6$ | $1.9 \times 10^6$ | $3.0 \times 10^6$ |
| 1 | $1.9 \times 10^6$ | $2.4 \times 10^6$ | $1.4 \times 10^6$ | $2.5 \times 10^6$ | $1.5 \times 10^6$ | $3.5 \times 10^6$ |
| 2 | $1.6 \times 10^6$ | $2.4 \times 10^6$ | $1.2 \times 10^6$ | $2.1 \times 10^6$ | $1.6 \times 10^6$ | $2.7 \times 10^6$ |
| 4 | $2.1 \times 10^6$ | $3.4 \times 10^6$ | $5.7 \times 10^6$ | $6.2 \times 10^6$ | $2.8 \times 10^6$ | $1.4 \times 10^5$ |
| 10 | $4.8 \times 10^6$ | $1.6 \times 10^7$ | $2.5 \times 10^7$ | $3.2 \times 10^7$ | $1.5 \times 10^7$ | $5.3 \times 10^5$ |
| 18 | $1.1 \times 10^7$ | $2.4 \times 10^6$ | $5.0 \times 10^5$ | $2.3 \times 10^6$ | $4.8 \times 10^6$ | $1.2 \times 10^7$ |

The above results clearly indicated that omission of malic acid in the propagation medium improved the survival of *Ln. oenos* strains when inoculated into a wine having a low pH (3.15) and a high ethanol content (11.5%). Therefore, further experiments were carried out to possibly identify the effects of the omission.

3.3. The Effect of pH of the Inoculum

Figure 3A:
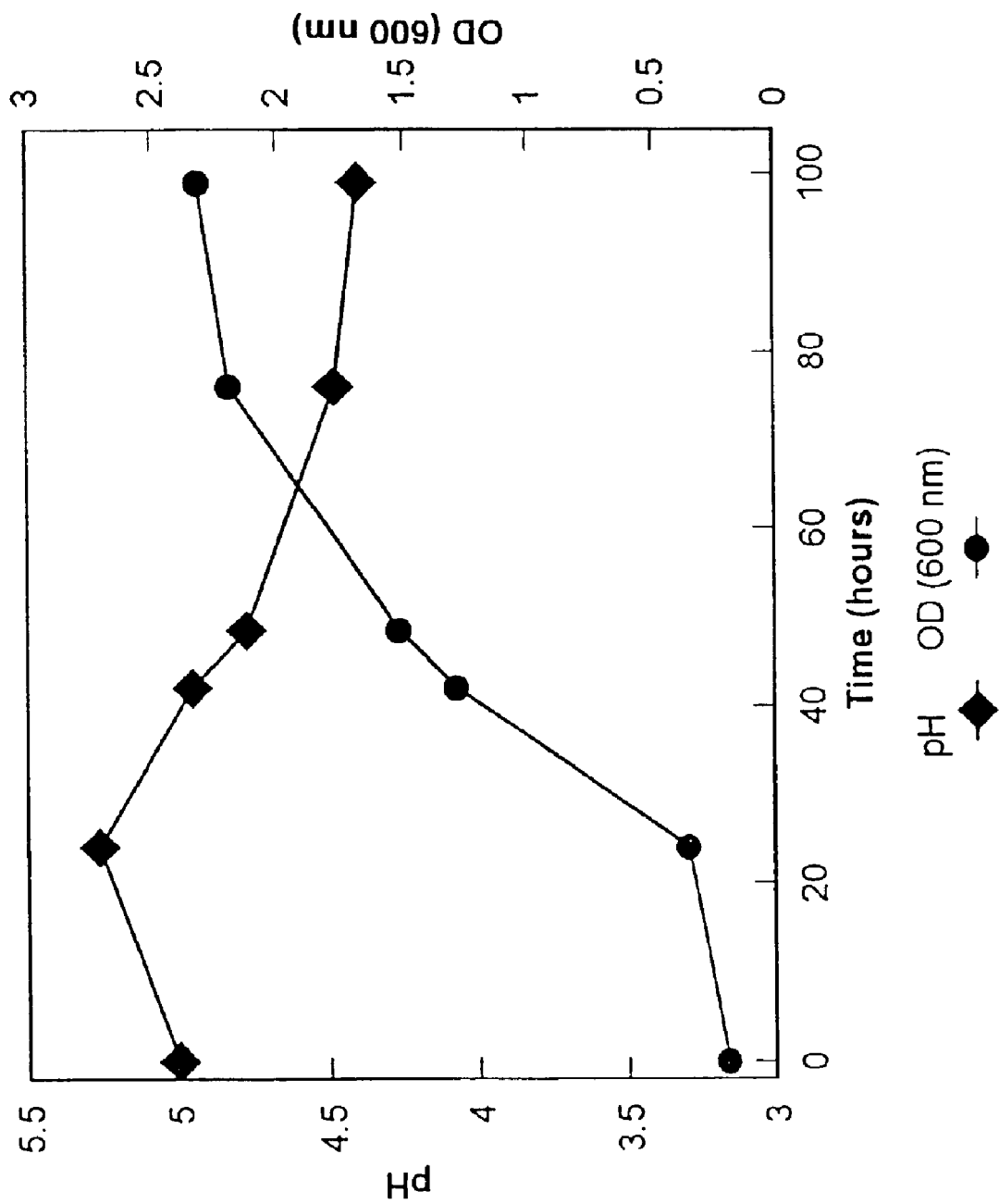
FIG. 3A shows the development in pH and $OD_{600}$ when *Ln. oenos* strain LOD 89004 is propagated in GJ-3 medium at 25° C.
Figure 3B:
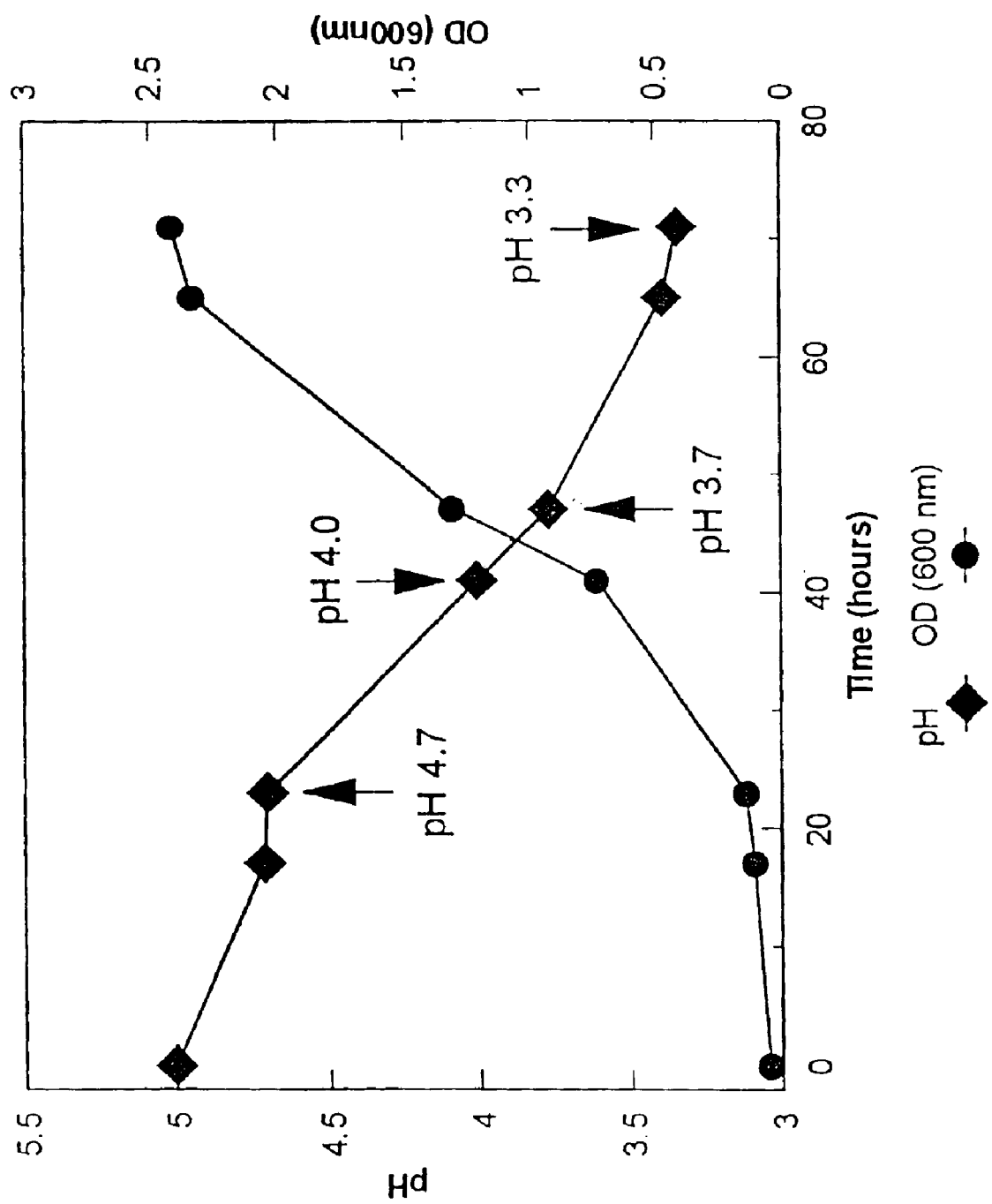
FIG. 3B shows the development in pH and $OD_{600}$ when *Ln. oenos* strain LOD 89004 is propagated in GJ-4 medium at 25° C. Samples were collected at different pH values as indicated by the arrows and used for inoculation into experimental wine.

FIGS. 3A and 3B illustrate the development in pH and $OD_{600}$ when strain LOD 89004 was propagated at 25° C. in GJ-3 and GJ-4, respectively. The final OD value in both media was 2.4. A relatively slow decline in pH was observed in GJ-3 and the final pH value was 4.4. In contrast, the pH in the GJ-4 medium decreased rapidly and reached a level of 3.3 after 3 days. This final pH value was considerably lower than that obtained in the above conventional GJ-3 medium under otherwise identical incubation conditions. It is contemplated that this difference is due to the fact that being a dicarboxylic acid malic acid has a considerable buffering capacity (pKa 5.1 and 3.4) implying that during cultivation in a medium containing malic acid pH will be lowered more slowly resulting in a higher final pH within the same incubation period.

During the propagation in GJ-4 medium, four samples were collected at intervals which are indicated by the arrows in FIG. 3B (at pH 4.71, 4.01, 3.77 and 3.34, respectively) and used as inocula into the experimental wine. The inoculated wine was kept at 20° C. for 20 days, samples were collected and CFU/ml was determined. The survival and growth in the wine of the four samples of LOD 89004 are summarized in Table 3.3 and FIG. 3C.

TABLE 3.3

CFU/ml in experimental wine inoculated with
*L. oenos* LOD 89004 propagated in GJ-4
and collected at different PH

| | pH in inoculum | | | |
|---|---|---|---|---|
| Day | 4.7 | 4.0 | 3.7 | 3.3 |
| 0 | $3.2 \times 10^5$ | $2.4 \times 10^6$ | $3.5 \times 10^5$ | $7.0 \times 10^5$ |
| 1 | $1.3 \times 10^4$ | $2.3 \times 10^5$ | $10.0 \times 10^5$ | $5.0 \times 10^5$ |
| 2 | $1.0 \times 10^3$ | $1.4 \times 10^5$ | $9.0 \times 10^5$ | |

TABLE 3.3-continued

CFU/ml in experimental wine inoculated with
*L. oenos* LOD 89004 propagated in GJ-4
and collected at different PH

| | pH in inoculum | | | |
|---|---|---|---|---|
| Day | 4.7 | 4.0 | 3.7 | 3.3 |
| 4 | | | | $8.1 \times 10^5$ |
| 5 | | $5.0 \times 10^4$ | $15.0 \times 10^5$ | |
| 6 | $1.0 \times 10^2$ | | | |
| 8 | | | | $75.0 \times 10^5$ |
| 9 | | $3.0 \times 10^4$ | $66.0 \times 10^5$ | |
| 10 | $1.0 \times 10^4$ | | | |
| 18 | | | | $180 \times 10^5$ |
| 19 | | $4.7 \times 10^6$ | $33.0 \times 10^5$ | |
| 20 | $1.8 \times 10^5$ | | | |

Figure 3C:
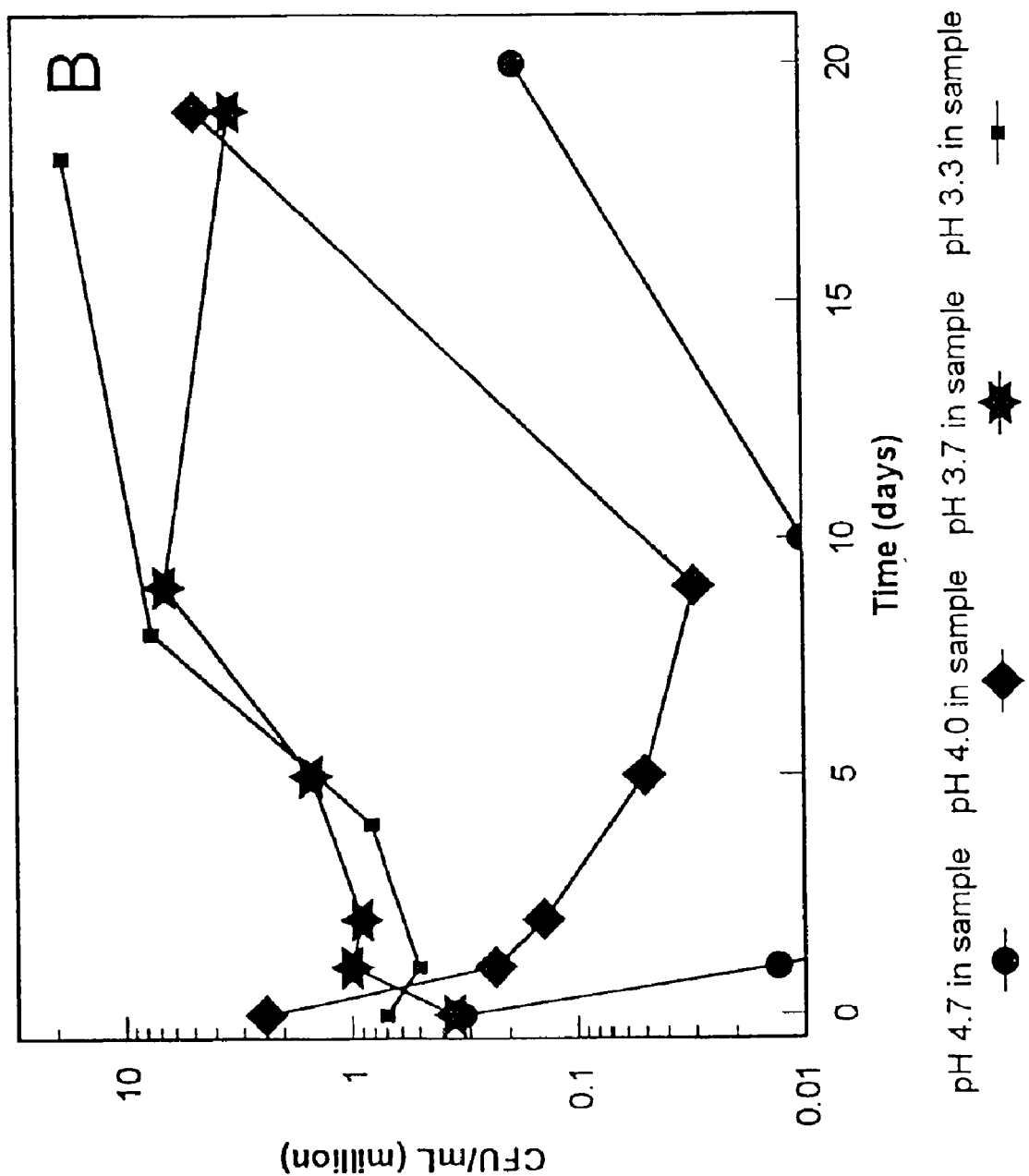
FIG. 3C shows the development in CFU/ml in an experimental wine, where the inocula were samples of *Ln. oenos* strain LOD 89004 propagated in GJ-4 and collected at different pH.

It appears from Table 3.3 and FIG. 3C that the LOD 89004 inocula having pH values of 3.7 and 3.3, respectively, when inoculated had the best survival in the wine and that growth was initiated almost immediately, whereas the number of viable cells initially declined rapidly in wine with the inocula with the higher pH values.

Thus, it could be concluded that the pH of the *Ln. oenos* culture at the time of inoculation into wine has a significant effect on its subsequent viability in the wine.

From FIG. 3B it can be seen that extending the propagation time from 41 hours to 47 hours at 25° C. resulted in a decrease of pH from 4.0 to 3.7. The ability of strain LOD 89004 to survive and grow in the wine was increased significantly over this 6 hours period. Further extension of the propagation time from 47 hours to 72 hours resulted in a decrease of pH to 3.3 in the medium, resulting in a further increase in the ability of the *Ln. oenos* strain to grow when inoculated into the experimental wine.

The effect of a low pH in the propagation medium on the ability of the strain to survive and grow in wine was largest when pH was decreased from about 4.0 to about 3.7, resulting in a propagation period at pH 4 or lower, of about 6 hours. An additional effect was obtained by further extending the propagation period to 72 hours, the effect mainly being on the ability of the strain to grow in the wine.

It is contemplated that this effect on survival and growth of the selected strains in wine is due to the maintenance of the adaptation of the strain to the low pH based on which they were originally selected.

It can also be concluded from the above experiments that a *Ln. oenos* strain which has been pre-selected on the basis of its ability to survive and grow well in wine will, when it is cultivated in a medium having a low buffering capacity such as the above GJ-4 medium, as a result of a propagation period in the medium at a pH of 4 or below for up to 31 hours, such as at least 6 hours, maintain its survival and growth characteristics based on which it was selected initially.

EXAMPLE 4

Optimization of *Ln. oenos* Biomass Yield

A number of factors including the pH of the production medium are known to affect the biomass yield in the production of selected lactic acid bacteria, i.e. a medium having a relatively high buffering capacity is generally preferred as acid(s) naturally produced by such bacteria will eventually inhibit their growth thereby limiting the biomass yield.

However, as it was shown in Example 3, a low pH of the propagation medium for *Ln. oenos* is essential for the ability of the selected strain to survive and grow when subsequently inoculated into wine. The implication hereof is that in an industrial production of *Ln. oenos* cultures for malolactic fermentation, the choice of the most appropriate initial pH in the strain production medium is a matter of compromise between two conflicting objectives, i.e. on the one hand to obtain a high biomass yield in the shortest possible time (favored by a relatively high pH) and on the other hand to achieve the best possible maintenance of characteristics based on which the strains were initially selected (favored by a relatively low pH).

Accordingly, the aims of the following experiments were to find an appropriate compromise between those two objectives.

4.1 Identification of Possible Growth Limiting Factors in GJ-3 Medium

Figure 4A:
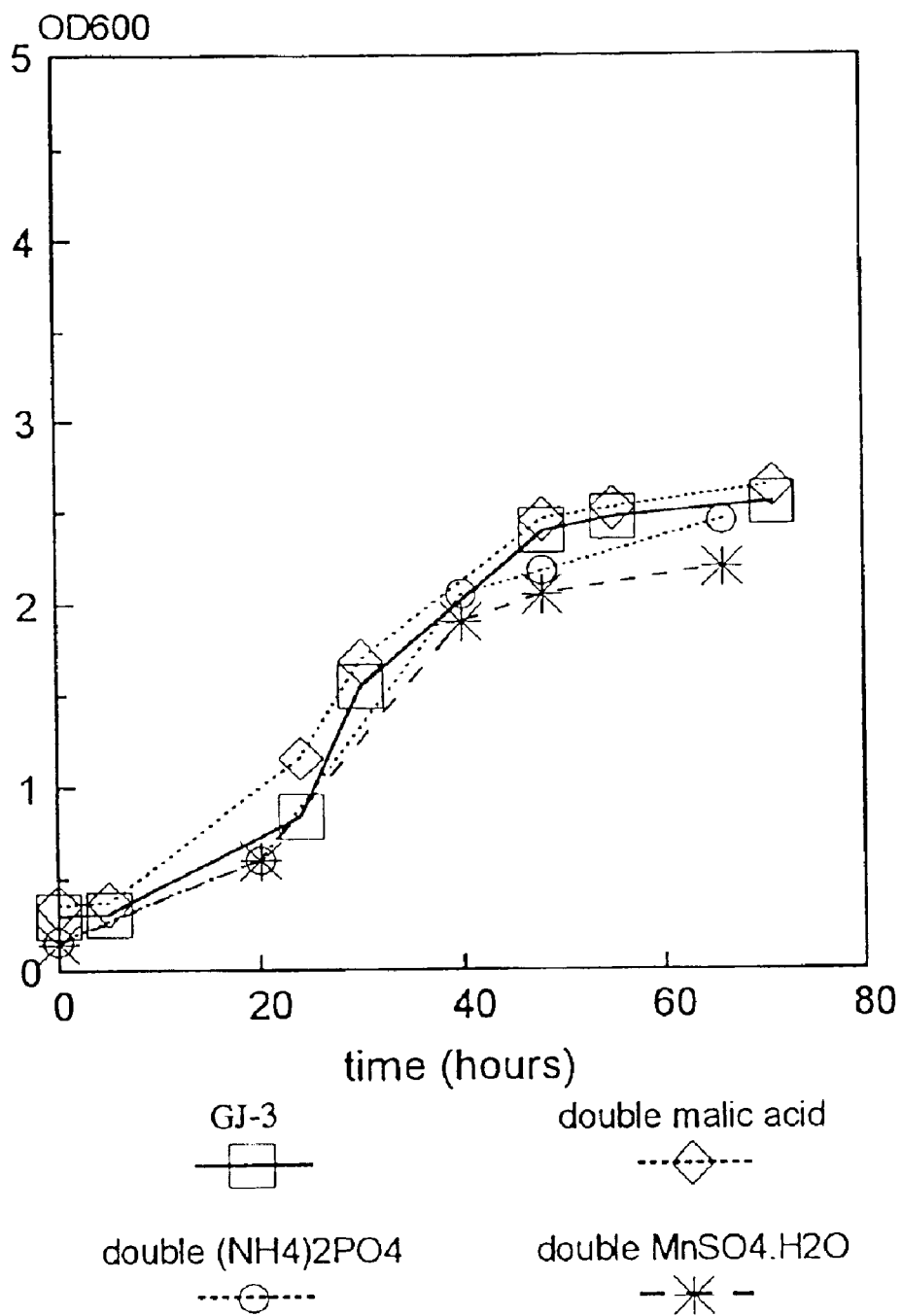
FIG. 4A shows the influence on $OD_{600}$ of doubling the amounts of each of the components DL-malic acid, $(NH_4)_2PO_4$ and $MnSO_4H_2O$.
Figure 4B:
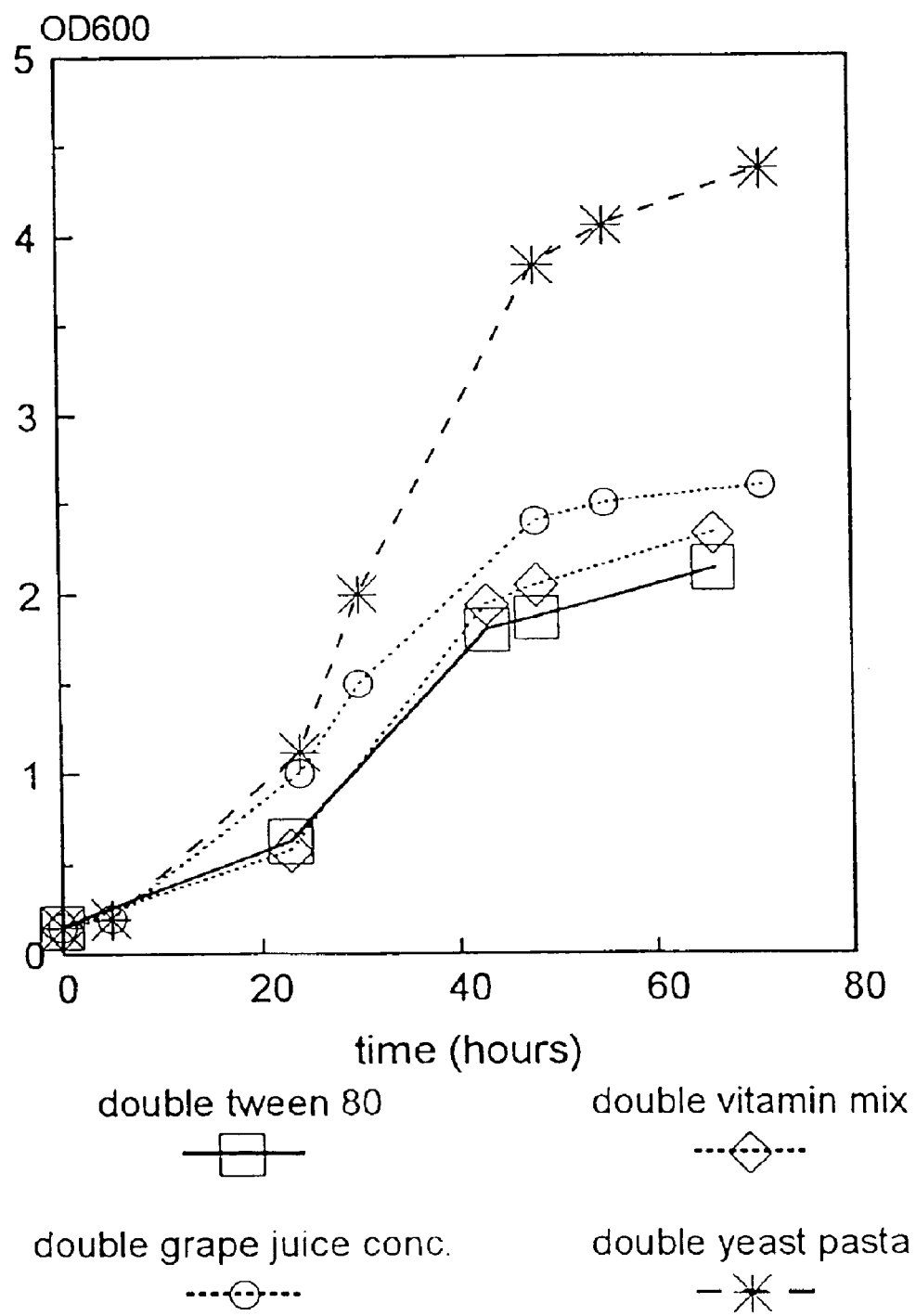
FIG. 4B shows the influence on $OD_{600}$ of doubling the amounts of each of the components yeast paste, Tween 80, grape juice concentrate and vitamin mixture.

To determine whether grape juice, yeast paste, DL-malic acid, $(NH_4)_2PO_4$, Tween 80, $MnSO_4H_2O$ or the vitamin mixture were limiting factors for the growth of the strain LOD 890004 in GJ-3 medium, the amount of each of these components were doubled one at time in a series of cultivation experiments. From the results (see FIGS. 4A and 4B) it could be concluded that of these components only yeast paste was a limiting factor for growth.

The optimal concentration of yeast paste was determined in a subsequent series of cultivations using concentrations of yeast paste in the range of 10 g/l to 35 g/l. It was found that growth rate and biomass yield increased with increasing concentrations of yeast paste. However, concentrations of yeast paste above 30 g/l resulted in an unacceptable precipitation in the medium and a high buffering capacity. Accordingly, GJ-3 medium was modified to contain 30 g/l yeast paste.

Cultivation experiments where the components other than yeast paste were omitted one by one from the modified GJ-3 medium showed that the presence of $(NH_4)_2PO_4$, vitamin mixture and DL-malic acid had no effect on the growth rate or the biomass yield. In the following experiments directed to optimizing the biomass yield, a medium based on the modified GJ-3 medium but without $(NH_4)_2PO_4$, vitamin mixture and DL-malic acid was used. Thus, this growth medium which was designated GJ-5 had the following composition:

| | |
|---|---|
| Grape juice concentrate | 70.0 g |
| Yeast paste | 30.0 g |
| Tween 80 | 0.5 g |
| $MnSO_4H_2O$ | 0.1 g |
| Tap water | 900.0 g |

4.2. Optimization of pH of the GJ-5 Medium

The pH of the GJ-5 medium was optimized with respect to obtaining a high growth rate and a high biomass yield of *Ln. oenos* while at the same time maintaining to a reasonably large extent the adaptation of the cultivated strains to the wine conditions already obtained during the preceding selection procedure.

Figure 4C:
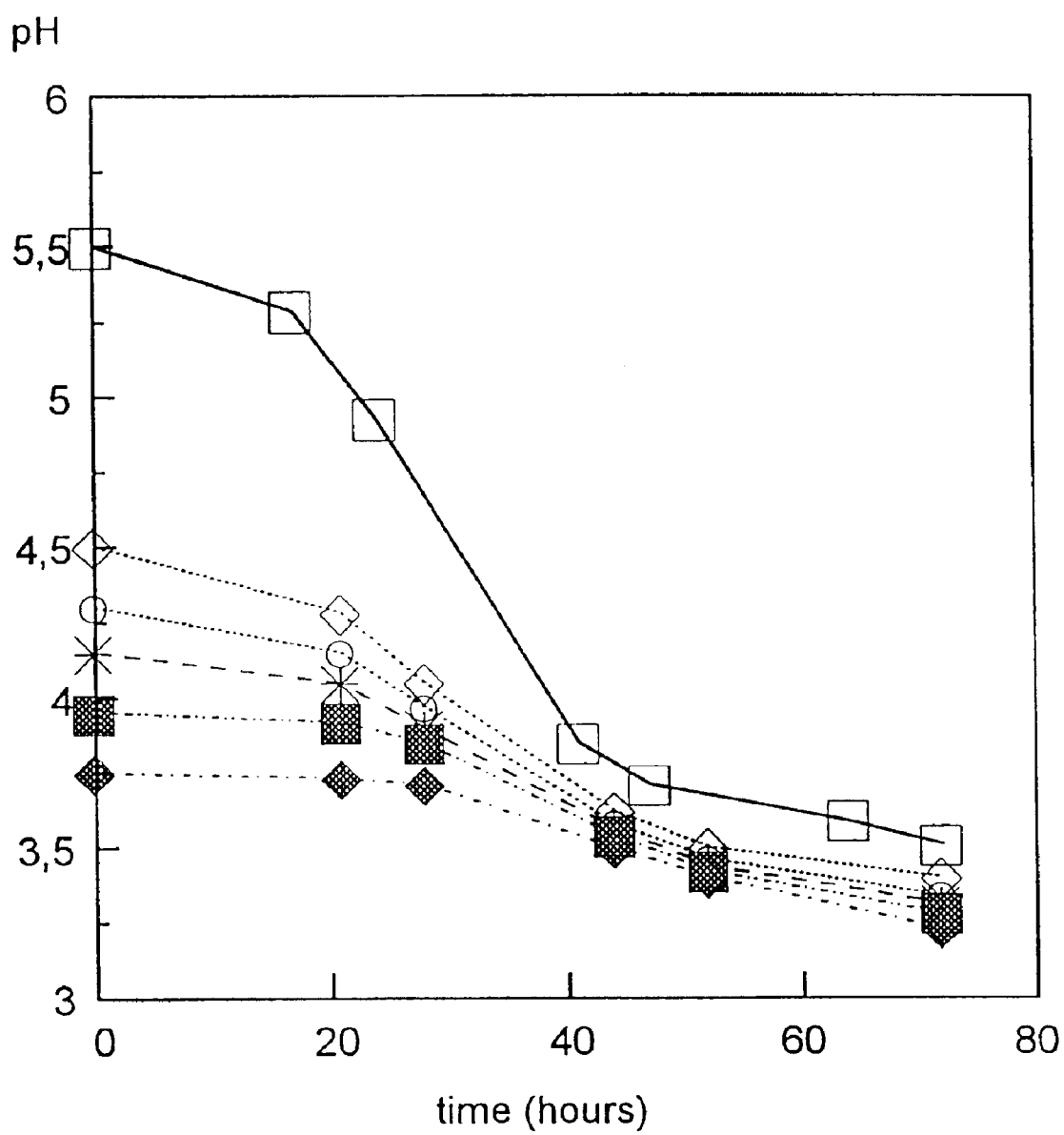
FIG. 4C shows the development in pH when *Ln. oenos* strain LOD 89004 is fermented in GJ-5 medium with initial pH values in the range of 3.75 to 5.5.
Figure 4D:
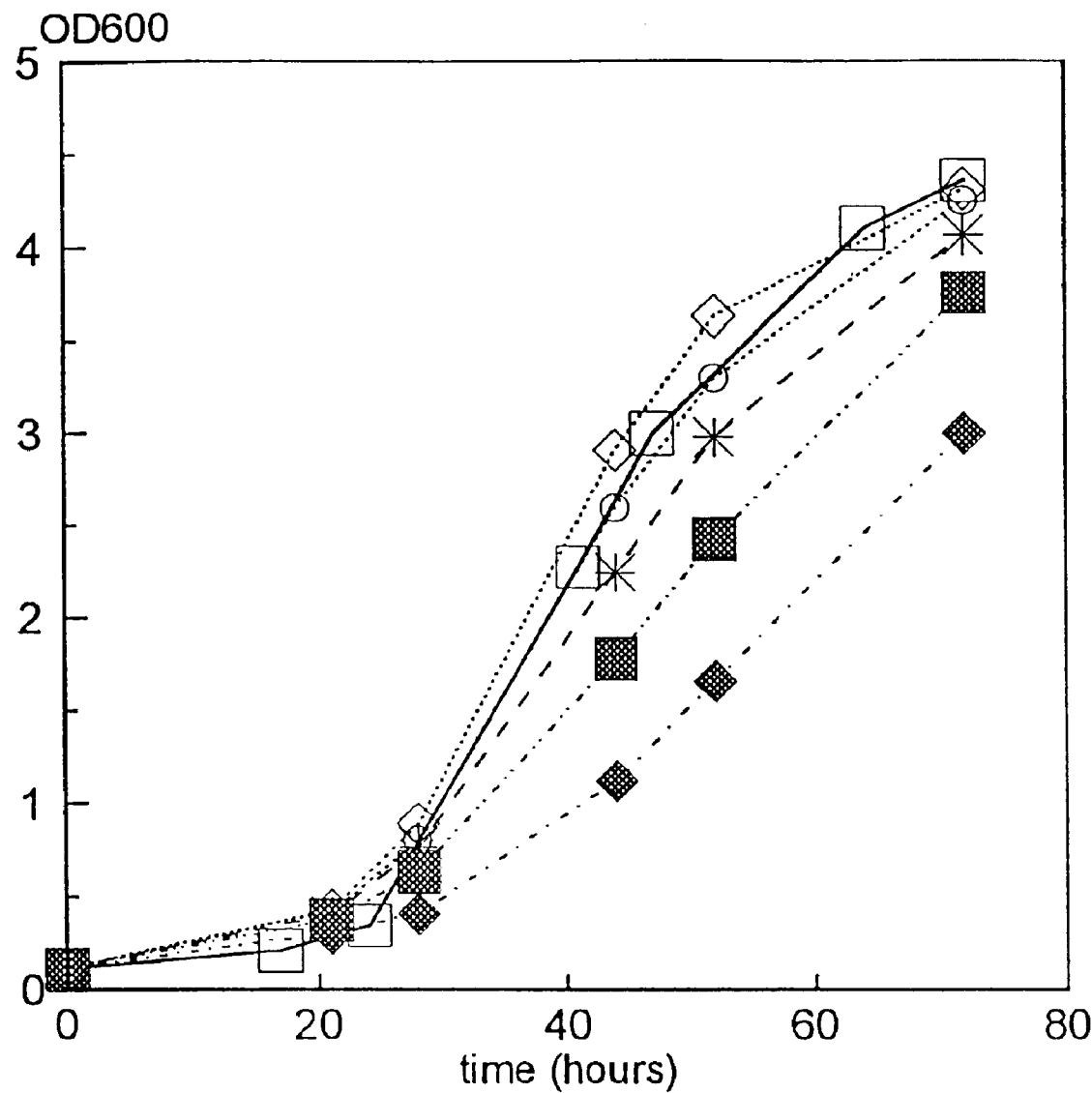
FIG. 4D shows the development in $OD_{600}$ when *Ln. oenos* strain LOD 89004 is fermented in GJ-5 medium with initial pH values in the range of 3.75 to 5.5.

Cultivations with initial pH values in the GJ-5 medium in the range of 3.75 to 5.5 were performed and the results are summarized in FIGS. 4C and 4D. A decrease in growth rate and biomass yield was found with decreasing pH. A pH of about 4 was reached for all of the cultivations except with initial pH of 5.5, within a period of about 30 hours of propagation at 25° C.

On this basis an initial pH value of 4.3 was selected for the GJ-5 medium for production purposes, since at this pH the biomass yield was essentially unaffected as compared to higher pH values and the desired pH below about 4 is reached well before the cultivation is completed, typical cultivation periods for *Ln. oenos* biomass production purposes being within the range of 40–60 hours.

4.3 Optimization of the Temperature of the Cultivation

The temperature used for cultivation in the GJ-5 medium was optimized with respect to obtaining a high growth rate.

Seven *Ln. oenos* strains, LOD 89004, LOD 89013, LOD 89017, LOD 89019, LOF 89103, LOF 89140 and LOF 89215, selected as described above, were inoculated into GJ-5 medium (initial pH 4.3) with a 1% inoculation level followed by propagation at temperatures of 28, 30, 32 and 34° C., respectively and the $OD_{600}$ of the cultures were measured at intervals. The generation times in the early exponential growth phase were calculated and the results are shown in Table 4.1.

TABLE 4.1

Generation time in hours of seven *Ln. oenos* strains cultivated in GJ-5 at 4 different temperatures.

| Strain | 28° C. | 30° C. | 32° C. | 34° C. |
|---|---|---|---|---|
| LOD 89004 | 4.5 | 4.2 | 4.0 | 4.5 |
| LOD 89013 | 5.0 | 4.4 | 4.1 | 4.5 |
| LOD 89017 | 4.8 | 4.5 | 4.1 | 4.9 |
| LOD 89019 | 4.5 | 4.3 | 3.8 | 4.3 |

TABLE 4.1-continued

Generation time in hours of seven Ln. oenos strains cultivated in GJ-5 at 4 different temperatures.

| Strain | 28° C. | 30° C. | 32° C. | 34° C. |
|---|---|---|---|---|
| LOD 89103 | 5.3 | 4.9 | 4.5 | 4.8 |
| LOD 89140 | 5.0 | 5.0 | 4.5 | 5.5 |
| LOD 89215 | 5.0 | 4.6 | 4.4 | 4.3 |

The optimum temperature for six of the seven Ln. oenos strains were in the range of 30 to 32° C. The outgrown cultures reached the maximum $OD_{600}$ at 30° C. within a period of 40 to 50 hours and at 32° C. within a period of 30–40 hours, respectively.

On this basis a temperature of 30° C. was selected for cultivation of Ln. oenos strain in GJ-5 medium with an initial pH of 4.3 and a cultivation period of 44 hours.

EXAMPLE 5

Inoculation of Frozen and Freeze-dried L. oenos into Wine or Fruit Juice

An isolated Ln. oenos strain according to the invention is frozen or freeze-dried using techniques that are well known in the art. Such a strain, when in a frozen or freeze-dried state, and added directly to wine or fruit juice without being prior-subjected to any step of activation, adaptation or expansion, has at least one of the characteristics i–iii:

(i) a survival rate which is in the range of 90% to 100% in a wine at a temperature in the range of 18 to 21° C., the wine having an ethanol content in the range of 10.5 to 13 vol %, a pH in the range of 3.2 to 3.6, and a content of $SO_2$ which is in the range of 0 to 26 mg per L; or (ii) a survival rate of at least 50% in a malic acid-containing wine having a pH of 3.2 or lower and containing at least 25 mg $SO_2$ per L and at least 12 vol % ethanol; or (iii) a survival rate which is in the range of from 80 to 100% after 2 days at a temperature of 20° C. in a wine prepared by yeasting a sterile Riesling grape fruit juice without the addition of sulphite, the wine having the characteristics of (a) containing approximately 11.5 vol % ethanol, (b) containing approximately 3.9 g/L of malic acid, (c) containing approximately 3.5 g/L of residual sugar, and (d) having a pH of 3.15.

What is claimed is:

1. A method of converting malic acid in a wine or a fruit juice to lactic acid, comprising adding directly to said wine or fruit juice a frozen or freeze-dried composition comprising a Ln. oenos strain, without any preceding activation, adaptation and/or expansion of the composition and keeping the wine or the fruit juice under conditions which allow conversion of the malic acid, to obtain a malolactically fermented wine or fruit juice having a content of malic acid which is at the most 0.5 g per l, wherein said Ln. oenos strain, when it is introduced into a wine containing at least 4 g of malic acid per liter, at a concentration of colony forming units which is in a range of $5 \times 10^6$ to $5 \times 10^7$ per ml of the wine, results in a malolactically fermented wine containing at the most 0.5 g malic acid per liter within a period which is at the most 15 days, wherein said Ln. oenos strain is malolactically active in wine or fruit juice and has at least one of the following characteristics when it in a freeze-dried state is added directly to wine without any preceding activation, adaptation and/or expansion step:

(i) a survival rate which is in the range of 90% to 100% in a wine at a temperature in the range of 18 to 21° C. said wine having an ethanol content in the range of 10.5 to 13 vol %. a pH in the range of 3.2 to 3.6 and a content of $SO_2$ which is in the range of 0 to 26 mg per l, or (ii) a survival rate of at least 50% in a malic acid-containing wine having a pH of 3.2 or lower and containing at least 25 mg $SO_2$ per l and at least 12 vol % ethanol, or (iii) a survival rate which is in the range of 80% to 100% after 2 days at a temperature of 20° C. in a wine prepared by veasting a sterile Riesling grape fruit juice without the addition of sulphite, the wine containing 11.5 vol % ethanol, 3.9 g/l of malic acid, 3.5 g/l of residual sugar and having a pH of 3.15.

2. A method according to claim 1 wherein the composition is added at a concentration of the malolactically active strain which is less than $10^7$ CFUs per ml of wine fruit juice.

3. A method according to claim 1 wherein the wine or the fruit juice to which the composition is added has a pH which is at the most 3.2.

4. A method according to claim 1 wherein the wine is selected from the group consisting of a red wine, a white wine and a sparking wine.

5. A method according to claim 1 wherein the selected malolactically active Ln. oenos strain has at least one of following characteristics:

(a) malolactically active in wine at a pH of 3.2 or lower,
(b) malolactically active in wine in the presence of 25 mg $SO_2$ per l or more.
(c) malolactically active in wine having an ethanol content of 10 vol % or higher,
(d) a survival rate of at least 50% when introduced into a wine having a pH of 3.2 or lower and containing at least 25 mg $SO_2$ per l and at least 12 vol % ethanol,
(e) resistant to attack by bacteriophages, or
(f) capable of retaining at least one of the characteristics (a) through (e) during propagation and concentration.

6. A method according to claim 5 wherein the selected strain has at least two of the characteristics (a) through (f).

7. A method according to claim 6 wherein the selected strain has at least three of the characteristics (a) through (f).

8. A method according to claim 7 wherein the selected strain has all of the characteristics (a) through (f).

9. A method according to claim 1 wherein the composition has a content of the malolactially active strain which is in the range of $10^9$ to $10^{13}$ colony forming units per g.

10. A method according to claim 9 wherein the composition has a content of the maloactically active strain which is in the range of $10^{10}$ to $10^{13}$ colony forming units per g.

11. A method according to claim 1 wherein the composition is added in an amount resulting in the introduction into the wine or fruit juice of a number of the maloactially active strain which is in the range of $10^5$ to $10^7$ colony forming units per ml.

12. A method according to claim 11 wherein the number of the malolactically active strain being introduced into the wine or the fruit juice is in the range of $10^6$ to $10^7$ colony forming units per ml.

13. A method according to claim 12 wherein the number of the malolactically active strain being introduced into the wine or the fruit juice is in the range of $5\times10^6$ to $10^7$ colony forming units per ml.

14. A method according to claim 1 wherein the wine or fruit juice has a content of malic acid which is at least 4 g per l.

15. A method according to claim 14 wherein the period of time to obtain the resulting malolactically fermented wine or fruit juice is at the most 15 days.

16. A method according to claim 15 wherein the period of time to obtain the resulting malolactically fermented wine or fruit juice is at the most 10 days.

17. A method according to claim 16 wherein the period of time to obtain the resulting malolactically fermented wine or fruit juice is at the most 8 days.

18. A method according to claim 1 wherein the wine or fruit juice has a content of malic acid which is at least 5.5 g per l.

19. A method din to claim 18 wherein the period of time to obtain the resulting malolactically fermented wine or fruit juice is at the most 15 days.

20. A method according to claim 19 wherein the period of time to obtain the resulting malolactically fermented wine or fruit juice is at the most 10 days.

21. A method according to claim 20, wherein the period of time to obtain the resulting malolactically fermented wine or fruit juice is at the most 8 days.

22. A method according to claim 1 wherein the obtained malolactically fermented wine or fruit juice has a content of malic acid which is at the most 0.1 g per l.

23. A method according to claim 1, wherein said *Ln. oenos* strain, when it is introduced into a wine containing at least 4 g of malic acid per liter, at a concentration of colony forming units is in a range of $5\times10^6$ to $5\times10^7$ per ml of the wine, results in a malolactically fermented wine containing at the most 0.5 g malic acid per liter within a period which is at the most 10 days.

* * * * *